US012723029B2

(12) United States Patent
Lisanti et al.

(10) Patent No.: US 12,723,029 B2

(45) Date of Patent: Sep. 1, 2026

(54) MITOCHONDRIAL ATP INHIBITORS TARGETING THE GAMMA SUBUNIT PREVENT METASTASIS

(71) Applicant: LUNELLA BIOTECH, INC., Ottawa (CA)

(72) Inventors: Michael P. Lisanti, Didsbury Village (GB); Federica Sotgia, Didsbury Village (GB); Marco Fiorillo, Manchester (GB); Jussi Kangasmetsa, Cambridge (GB)

(73) Assignee: LUNELLA BIOTECH, INC., Ontario (CA)

( * ) Notice: Subject to any disclaimer, the term of this patent is extended or adjusted under 35 U.S.C. 154(b) by 459 days.

(21) Appl. No.: 18/033,266

(22) PCT Filed: Oct. 22, 2021

(86) PCT No.: PCT/IB2021/059772

§ 371 (c)(1),
(2) Date: Apr. 21, 2023

(87) PCT Pub. No.: WO2022/084947

PCT Pub. Date: Apr. 28, 2022

(65) Prior Publication Data

US 2024/0010622 A1 Jan. 11, 2024

Related U.S. Application Data

(60) Provisional application No. 63/104,160, filed on Oct. 22, 2020.

(51) Int. Cl.

| | |
|---|---|
| *C07D 215/227* | (2006.01) |
| *A61K 31/47* | (2006.01) |
| *A61K 47/54* | (2017.01) |
| *A61P 35/04* | (2006.01) |
| *C12Q 1/6869* | (2018.01) |
| *C12Q 1/6886* | (2018.01) |

(52) U.S. Cl.

CPC .......... *C07D 215/227* (2013.01); *A61K 31/47* (2013.01); *A61K 47/542* (2017.08); *A61P 35/04* (2018.01); *C12Q 1/6869* (2013.01); *C12Q 1/6886* (2013.01); *C12Q 2600/158* (2013.01)

(58) Field of Classification Search

None

See application file for complete search history.

(56) References Cited

U.S. PATENT DOCUMENTS

| | | |
|---|---|---|
| 8,415,475 B2 | 4/2013 | Guillemont et al. |
| 2020/0255902 A1 | 8/2020 | Lisanti et al. |

FOREIGN PATENT DOCUMENTS

| | | |
|---|---|---|
| WO | 2008068267 A1 | 6/2008 |
| WO | 2018213751 A1 | 11/2018 |
| WO | WO 2021/048830 A1 | 3/2021 |
| WO | 2021214727 A1 | 10/2021 |

OTHER PUBLICATIONS

Chambers. Journal of Molecular Medicine, 2015, 93, 261-368 (Year: 2015).*

Bedaquiline, an FDA-approved drug, inhibits mitochondrial ATP-production and metastasis in vivo, by targeting the gamma subunit (ATP5F1C) of the ATP synthase, Marco Fiorillo, 等, «Cell Death & Differentiation», 第 28 卷, 第 2797-2817.

Bedaquiline, an FDA-approved drug, inhibits mitochondrial function and potently blocks the proliferative expanion of stem-like cancer cells (CSCs), Marco Fiorillo, 等, «Aging [electronic resource]», 第 8卷, 第 8 期, 第 1593-1607.

Min Luo, et al., Bedaquiline inhibits the Yeast and Human Mitochondrial ATP Synthases.

International Search Report and Written Opinion of the ISA dated Feb. 8, 2022, for PCT/IB2021/059772, 15 pp.

William A. Denny, "Inhibitors of F1F0-ATP synthase enzymes for the treatment of tuberculosis and cancer", Future Medicinal Chemistry, vol. 13, No. 10, Apr. 13, 2021, pp. 911-926.

Marco Fiorillo et al., "High ATP Productoin Fuels Cancer Drug Resistance and Metastasis: Implications for Mitochondrial ATP Depletion Therapy", Frontiers in Oncology, vol. 11, article 740720, Oct. 15, 2021, pp. 1-11.

Xiaomu Wu et al., "Antibiotic bedaquiline effectively targets growth, survival and tumor angiogenesis of lung cancer through suppressing energy metabolism", Biochemical and Biophysical Research Communications, vol. 495, Oct. 28, 2017, pp. 267-272.

Edith Emmings et al., "Targeting Mitochondria for Treatment of Chemoresistant Ovarian Cancer", International Journal of Molecular Sciences, vol. 20, No. 229, Jan. 8, 2019, pp. 1-14.

Amy S. T. Tong et al., "6-Cyano Analogues of Bedaquiline as Less Lipophilic and Potentially Safer Diarylquinolines for Tuberculosis", ACS Medicinal Chemistry Letters, vol. 8, Sep. 22, 2017, pp. 1019-1024.

Registry Copyright 2025 ACS on STN registry No. RN2144501-98-2 issued Nov. 20, 2017.

* cited by examiner

*Primary Examiner* — Noble E Jarrell

(74) *Attorney, Agent, or Firm* — Nixon & Vanderhye, P.C.

(57) ABSTRACT

High ATP production by the mitochondrial ATP-synthase is a new therapeutic target for anti-cancer therapy, especially for preventing tumor progression. A mitochondrial-related gene signature for metastasis is described, which features the gamma-subunit of the mitochondrial ATP-synthase (ATP5F1C). Knock-down of ATP5F1C expression significantly reduces ATP-production, 3D anchorage-independent growth and cell migration. Administration of the Bedaquiline, or a Bedaquiline derivative with a fatty acid moiety, down-regulates ATP5F1C expression in vitro and prevents spontaneous metastasis in vivo. Mitochondrial ATP5F1C is a promising new biomarker and molecular target for future drug development, for the prevention of metastatic disease progression.

8 Claims, 18 Drawing Sheets

Genes correlated with ATP5F1C (n=146)

| Correlated Gene | Cytoband | Spearman's Correlation | p-Value | q-Value |
|---|---|---|---|---|
| UQCRB | 8q22.1 | 0.457 | 6.89E-09 | 2.43E-07 |
| COX20 | 1q44 | 0.232 | 4.78E-03 | 0.022 |

| Symbol | Accession | Expr Fold Change MCF7 Spheres Vs Adh. | Expr Fold Change T47D Spheres Vs Adh. |
|---|---|---|---|
| ABCF3 | B4DRU9 | 358.862 | 3.849 |
| ATP13A2 | Q8NBS1 | 560.751 | 42.918 |
| ATP13A4 | H7C1P5 | 20.517 | 25.583 |
| ATP1A1 | B7Z3V1 | 51.419 | 14.905 |
| ATP1A3 | P13637 | 229.056 | 16.789 |
| ATP1A4 | Q13733 | 440.915 | 60.871 |
| ATP1B1 | A3KLL5 | 1.913 | 10.585 |
| ATP1B3 | P54709 | 12.082 | 3.433 |
| ATP2A2 | P16615 | 20.838 | 7.006 |
| ATP2A3 | Q93084 | 78.477 | 23.288 |
| ATP2B1 | E7ERY9 | 7.655 | 2.928 |
| ATP5F1B | Q0QEN7 | 10.129 | 2.087 |
| ATP5F1C | Q8TAS0 | 1.947 | 1.634 |
| ATP5IF1 | Q9UII2 | 10.127 | 16.359 |
| ATP5MG | O75964 | 1.819 | 1.429 |
| ATP5PB | Q53GB3 | 2.515 | 4.379 |
| ATP5PD | O75947 | 2.27 | 1.436 |
| ATP5PO | P48047 | 1.82 | 1.426 |
| COX5B | P10606 | 7.692 | 1.513 |
| NDUFAB1 | H3BNK3 | 87.149 | 11.85 |
| UQCR10 | Q9UDW1 | 2.457 | 1.623 |
| UQCRH | Q567R0 | 1.662 | 2.171 |

MITOCHONDRIAL ATP INHIBITORS TARGETING THE GAMMA SUBUNIT PREVENT METASTASIS

CROSS-REFERENCE TO RELATED APPLICATIONS

This application is the U.S. national phase of International Application No. PCT/IB2021/059772 filed Oct. 22, 2021, which designated the U.S. and claims the benefit of provisional application U.S. 63/104,160 filed Oct. 22, 2020, the entire contents of each of which are hereby incorporated by reference.

FIELD

The present disclosure relates to inhibiting mitochondrial ATP to prevent or reduce the likelihood of metastasizing cancer stem cells (CSCs).

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Sotgia et al., *Cell Cycle,* 11 (23): 4390-4401 (2012). Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis. Lamb et al., *Oncotarget,* 5 (22): 11029-11037 (2014).

Mitochondria are extremely dynamic organelles in constant division, elongation and connection to each other to form tubular networks or fragmented granules in order to satisfy the requirements of the cell and adapt to the cellular microenvironment. The balance of mitochondrial fusion and fission dictates the morphology, abundance, function and spatial distribution of mitochondria, therefore influencing a plethora of mitochondrial-dependent vital biological processes such as adenosine triphosphate (ATP) production, mitophagy, apoptosis, and calcium homeostasis. In turn, mitochondrial dynamics can be regulated by mitochondrial metabolism, respiration and oxidative stress.

ATP is the universal bioenergetic "currency" of all living cells and tissues, including microorganisms, such as prokaryotic bacteria and eukaryotic yeast. In eukaryotes, mitochondrial organelles function as the "powerhouse" of the cell. Mitochondria generate the vast amount of ATP via the TCA cycle and oxidative phosphorylation (OXPHOS), while glycolysis contributes a minor amount of ATP. Conversely, mitochondrial dysfunction induces ATP-depletion, resulting in mitochondrial-driven apoptosis (programmed cell death) and/or necrosis. Thus, we have proposed that ATP-depletion therapy may be a viable strategy for targeting and eradicating even the "fittest" cancer cells.

In MCF7 breast cancer cells, mitochondrial-driven OXPHOS contributes to 80-90% of ATP production, while glycolysis only contributes the remaining 10-20%, under normoxic conditions. Therefore, like normal cells, cancer cells are highly dependent on mitochondrial ATP production. However, it still remains largely unknown if ATP levels in cancer cells contribute to undergo 3D anchorage-independent growth and cell migration, two characteristic features of metastatic spread.

It is an object of this disclosure to identify a new therapeutic target for anti-cancer therapy, and in particular, for preventing tumor progression. It is another object of this disclosure to identify compounds having anti-cancer activity, and in particular, for preventing and/or reducing the likelihood of tumor recurrence and/or metastasis. It is another object of this disclosure to provide companion diagnostics relating to the therapeutic target.

SUMMARY

In view of the foregoing background, it is an object of this disclosure to describe therapeutic agents that may be used to eradicate CSCs. It is further an object of this disclosure to describe compositions, such as pharmaceutical compositions, and methods for treating and preventing cancer.

Bedaquiline (a.k.a., Sirturo) is an FDA-approved antibiotic that is clinically used for the treatment of drug-resistant tuberculosis. Originally, it was thought that Bedaquiline only affected the myco-bacterial ATP-synthase, but the inventors' studies have shown that Bedaquiline also potently inhibits the yeast and human mitochondrial ATP-synthase. High resolution cryo-EM studies have shown that Bedaquiline binds directly to the gamma-subunit (ATP5F1C) that forms the rotary shaft of the mitochondrial ATP-synthase, which is critically involved in torque transmission, ultimately providing the necessary mechano-chemical energy for ATP-synthesis.

As shown herein, the binding of Bedaquiline to ATP5F1C leads to the degradation of ATP5F1C in living cells. Bedaquiline induces the down-regulation of ATP5F1C protein expression, with concomitant mitochondrial ATP-depletion, in both a time- and concentration-dependent manner. Furthermore, ATP-depletion induced by Bedaquiline treatment effectively blocks spontaneous metastasis in vivo, without significant toxicity in non-tumorigenic human cells (MCF10A) or chicken embryos.

Under the present approach, the gamma-subunit of the mitochondrial ATP-synthase (ATP5F1C) is identified as a new therapeutic target, for mitigating aggressive cancer cell behaviors, including tumor recurrence and/or metastasis.

Described herein is the use of (1R,2S)-1-(6-bromo-2-methoxyquinolin-3-yl)-4-(dimethylamino)-2-naphthalen-1-yl-1-phenylbutan-2-ol, also known as Bedaquiline, an FDA-approved drug, and analogs thereof, to induce ATP-depletion in cancer cells. In laboratory experiments, Bedaquiline effectively induced ATP-depletion in MDA-MB-231 breast cancer cells. For example, an 8-day treatment with Bedaquiline was sufficient to prevent the onset of spontaneous metastasis in in vivo xenograft models, without affecting tumor growth. Bedaquiline and certain analogs thereof specifically target ATP5F1C, the gamma-subunit of the mitochondrial ATP-synthase. This target is consistent with the ATP5F1C being a functional biomarker and therapeutic target for metastasis prevention.

Also described herein are Bedaquiline derivatives having a fatty acid moiety. These compounds induce ATP-depletion in CSCs and effectively prevent and/or reduce the likelihood of tumor recurrence and/or metastasis. The Bedaquiline derivatives are more potent than Bedaquiline, are selective towards CSCs, and are non-toxic to normal, healthy cells.

The present approach may also be used to treat and/or prevent tumor recurrence and/or metastasis. Anti-cancer treatments often fail because the tumor recurs or metastasizes, particularly after surgery. CSC mitochondrial activity is understood to be, at least in part, responsible for these causes of treatment failure. Embodiments of the present approach may be used in situations where conventional cancer therapies fail, and/or in conjunction with or prior to anti-cancer treatments, to prevent or reduce the likelihood of treatment failure due to tumor recurrence and/or metastasis.

Some embodiments of the present approach may take the form of methods for treating or preventing at least one of tumor recurrence and metastasis in a subject. The method involves administering to the subject a pharmaceutically effective amount of Bedaquiline or a Bedaquiline derivative with a fatty acid. Various Bedaquiline derivatives are disclosed.

In some embodiments, the Bedaquiline derivative has the general formula

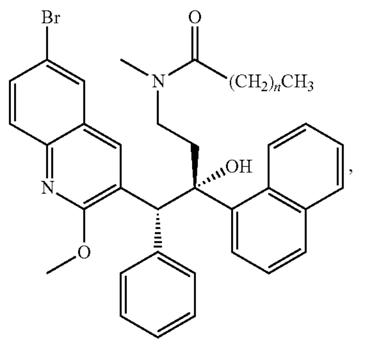

wherein n is an integer from 3 to 18.

In some embodiments, the Bedaquiline derivative has the general formula

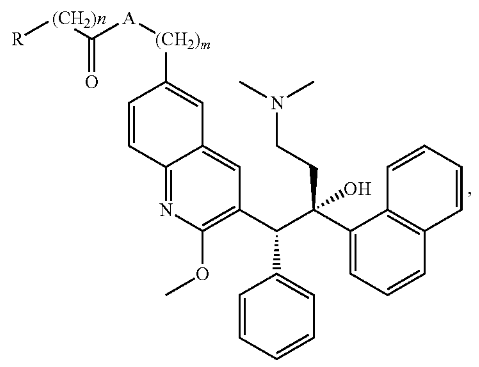

wherein R is selected from the group consisting of H, substituted or unsubstituted C1-C6 straight alkyl, substituted or unsubstituted C1-C6 branched alkyl, substituted or unsubstituted aryl, substituted or unsubstituted heteroaryl, substituted or unsubstituted cycloalkyl, substituted or unsubstituted heterocycle; n is an integer from 1 to 18; m is an integer from 1 to 12; and A is absent or is selected from C, O, N, or S, protonated as necessary to satisfy valence.

In some embodiments, the Bedaquiline derivative has the general formula

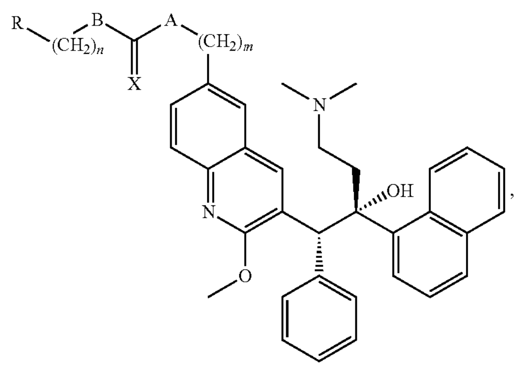

wherein R is selected from the group consisting of H, substituted or unsubstituted C1-C6 straight alkyl, substituted or unsubstituted C3-C6 branched alkyl, substituted or unsubstituted aryl, substituted or unsubstituted heteroaryl, substituted or unsubstituted cycloalkyl, substituted or unsubstituted heterocycle; n is an integer from 1 to 18; m is an integer from 1 to 12; A is absent or selected from C, O, N, or S, protonated as necessary to satisfy valence; and B is absent or selected from C, O, N, or S, protonated as necessary to satisfy valence.

In some embodiments, the present approach may take the form of methods for preventing and/or reducing the likelihood of tumor metastasis and tumor recurrence in a patient. A biological sample of a cancer from the patient may be obtained. The level of biomarkers in the biological sample of an ATP-related metastasis gene-signature consisting of ABCA2, ATP5F1C, COX20, NDUFA2 and UQCRB may be determined, and compared a threshold level. If the determined level exceeds the threshold level, then a pharmaceutically effective amount of a composition containing Bedaquiline or a Bedaquiline derivative with a fatty acid may be administered.

DESCRIPTION

Figure 1A:
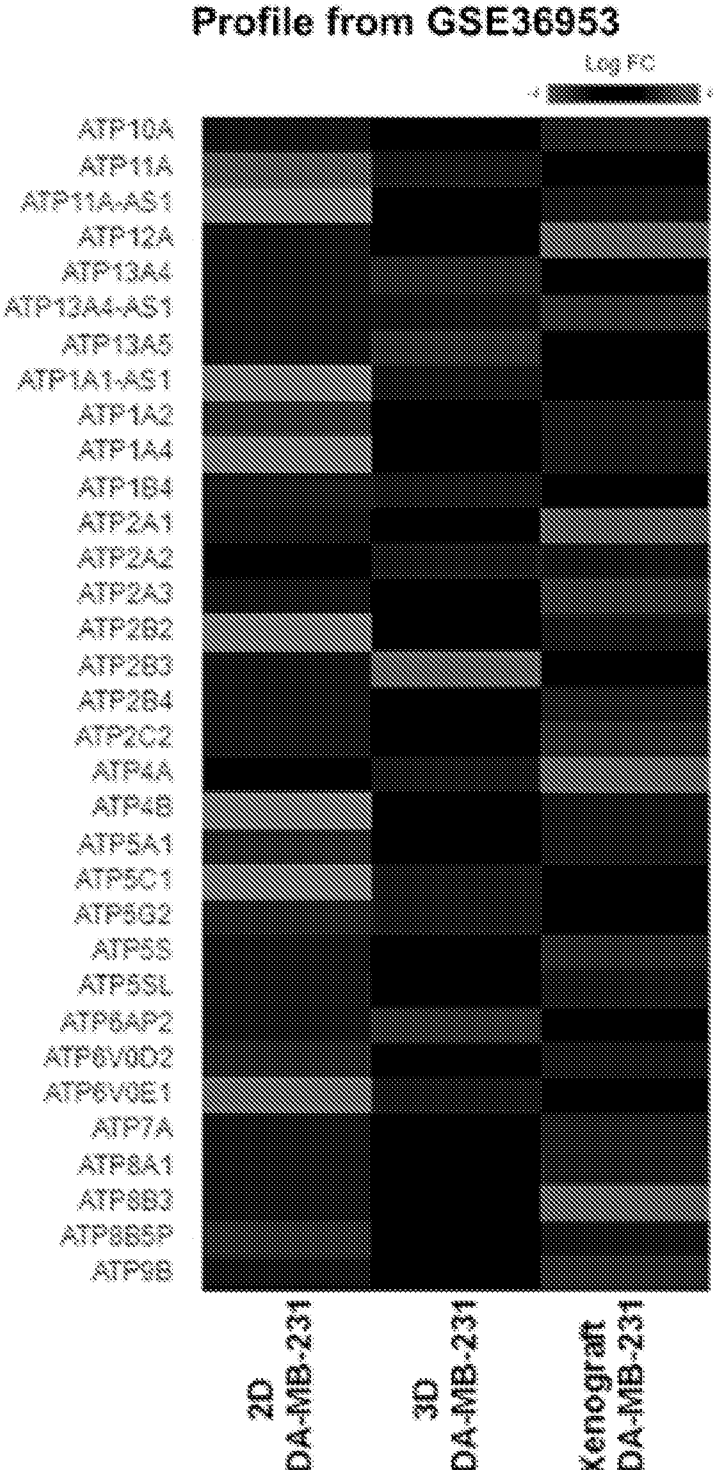
FIG. 1A illustrates a HeatMap comparing the transcriptional profiles of ATP-related genes (OXPHOS and ATP-related transporters).

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

This description uses various terms that should be understood by those of an ordinary level of skill in the art. The following clarifications are made for the avoidance of doubt.

The term "cancer" refers to physiological conditions in mammals that are typically characterized by uncontrolled cell growth. This definition includes benign and malignant cancers. Examples of cancers include cancer types, lymphomas, blastomas (including medullablastomas and retinoblastomas), sarcomas (including liposarcomas and synovial sarcomas), neuroendocrine tumors (carcinoid tumors, gastrin production Includes, but is not limited to, tumors and islet cell carcinomas), sarcomas, Schwannomas (including acoustic neuroma), medullary carcinomas, adenocarcinomas, melanomas, and leukemia or lymphocyte tumors. Specific examples of cancers include bladder cancer, squamous cell carcinoma, small cell lung cancer, non-small cell lung cancer, lung adenocarcinoma, and lung cancer including squamous epithelial cancer of the lung, peritoneal cancer, hepatocellular carcinoma, gastric cancer including gastrointestinal cancer or stomach cancer, pancreatic cancer, glioblastoma, cervical cancer, ovarian cancer, liver cancer, bladder cancer, liver cancer, breast cancer (including metastatic breast cancer), colon cancer, rectal cancer, colon rectal cancer, endometrial cancer or uterine cancer, salivary adenocarcinoma, kidney cancer (kidney cancer) or kidney cancer (renal cancer), prostatic cancer, genital cancer, thyroid cancer, liver cancer, anal cancer, penis cancer, testicular cancer, esophageal cancer, bile duct tumor, and head and neck cancer and multiple myeloma.

As used herein, the term "tumor" refers to the growth and proliferation of neoplastic cells, whether malignant or benign, including pre-cancerous and cancerous cells and tissues.

The term "metastasis" refers to the spread of cancer from its primary site to other parts of the body. Cancer cells can escape from the primary tumor, penetrate lymph vessels and blood vessels, circulate through the bloodstream, and grow or "metastasize" in distant lesions in normal tissue elsewhere in the body. Metastases can be local or distant. Metastasis is a sequential process that requires tumor cells to escape from the primary tumor, travel through the bloodstream, and stop at distant sites. At this new site, cells can establish a blood supply and grow to form a life-threatening mass. Both irritating and inhibitory molecular pathways within tumor cells control this behavior, and the interaction between tumor cells and host cells at distant sites is also important.

The terms "treat," "treated," "treating," and "treatment" include the diminishment or alleviation of at least one symptom associated or caused by the state, disorder or disease being treated, in particular, cancer. In certain embodiments, the treatment comprises diminishing and/or alleviating at least one symptom associated with or caused by the cancer being treated, by the compound of the invention. In some embodiments, the treatment comprises causing the death of a: category of cells, such as CSCs likely to be involved in metastasis or recurrence, of a particular cancer in a host, and may be accomplished through preventing cancer cells from further propagation, and/or inhibiting CSC function through, for example, depriving such cells of mechanisms for generating energy. For example, treatment can be diminishment of one or several symptoms of a cancer, or complete eradication of a cancer. As another example, the present approach may be used to inhibit mitochondrial metabolism in the cancer, eradicate (e.g., killing at a rate higher than a rate of propagation) CSCs in the cancer, eradicate TICs in the cancer, eradicate circulating tumor cells in the cancer, inhibit propagation of the cancer, target and inhibit CSCs, target and inhibit TICs, target and inhibit circulating tumor cells, prevent or reduce the likelihood of, metastasis, prevent recurrence, sensitize the cancer to a chemotherapeutic, sensitize the cancer to radiotherapy, sensitize the cancer to phototherapy.

In the context of tumor recurrence and/or metastasis, the term "prevent" and "reduce the likelihood of" refer to reducing, in a subject, the presence of CSCs, TICs, and circulating tumor cells, likely to be involved in recurrence or metastasis, to a level at which tumor recurrence and/or metastasis from the primary site is unlikely, relative to a control (i.e., no treatment to prevent or reduce the likelihood of tumor recurrence and/or metastasis). In practice, a treatment to prevent and/or reduce the likelihood of tumor recurrence and/or metastasis as described herein targets and inhibits or eradicates CSCs, TICs, inhibit circulating tumor cells.

The terms "cancer stem cell" and "CSC" refer to the subpopulation of cancer cells within tumors that have capabilities of self-renewal, differentiation, and tumorigenicity when transplanted into an animal host. Compared to "bulk" cancer cells, CSCs have increased mitochondrial mass, enhanced mitochondrial biogenesis, and higher activation of mitochondrial protein translation. As used herein, a "circulating tumor cell" is a cancer cell that has shed into the vasculature or lymphatics from a primary tumor and is carried around the body in the blood circulation. The CellSearch Circulating Tumor Cell Test may be used to detect circulating tumor cells.

The phrase "pharmaceutically effective amount," as used herein, indicates an amount necessary to administer to a host, or to a cell, tissue, or organ of a host, to achieve a therapeutic result, such as regulating, modulating, or inhibiting protein kinase activity, e.g., inhibition of the activity of a protein kinase, or treatment of cancer. A physician or veterinarian having ordinary skill in the art can readily determine and prescribe the effective amount of the pharmaceutical composition required for a given subject, using methods well-known and available in the art. For example, the physician or veterinarian could start doses of the compounds of the invention employed in the pharmaceutical composition at levels lower than that required in order to achieve the desired therapeutic effect and gradually increase the dosage until the desired effect is achieved.

As used herein, the phrase "active compound" refers to Bedaquiline or the Bedaquiline derivative compounds described herein, which may include a pharmaceutically acceptable salt or isotopic analog thereof. It should be appreciated that the active compound(s) may be administered to the subject through any suitable approach, as would be known to those having an ordinary level of skill in the art. It should also be appreciated that the amount of active compound and the timing of its administration may be dependent on the individual subject being treated (e.g., the age and body mass, among other factors), on the manner of administration, on the pharmacokinetic properties of the particular active compound(s), and on the judgment of the prescribing physician. Thus, because of subject to subject variability, any dosages described herein are intended to be initial guidelines, and the physician can titrate doses of the compound to achieve the treatment that the physician considers appropriate for the subject. In considering the degree of treatment desired, the physician can balance a variety of factors such as age and weight of the subject, presence of preexisting disease, as well as presence of other diseases. Pharmaceutical formulations can be prepared for any desired route of administration including, but not limited to, oral, intravenous, or aerosol administration, as discussed in greater detail below.

The phrase "pharmaceutically acceptable carrier" as used herein, means a pharmaceutically acceptable material, composition, or vehicle, such as a liquid or solid filler, diluent, excipient, solvent, or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose: (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "derivative" is a chemical moiety derived or synthesized from a referenced chemical moiety. For example, compounds according to the present approach may be referred to as Bedaquiline derivatives, and have a fatty acid moiety conjugated at either the 6-bromo position or the dimethylamino.

As used herein, a "fatty acid" moiety is a carboxylic acid with an aliphatic chain, which is either saturated or unsaturated. Examples of fatty acids include short chain fatty acids (i.e., having 5 or fewer carbon atoms in the chemical structure), medium-chain fatty acids (having 6-12 carbon atoms in the chemical structure), and other long chain fatty acids (i.e., having 13-21 carbon atoms in the chemical structure). Examples of saturated fatty acids include lauric acid ($CH_3(CH_2)_{10}COOH$), palmitic acid ($CH_3(CH_2)_{14}COOH$), stearic acid ($CH_3(CH_2)_{16}COOH$), and myristic acid ($CH_3(CH_2)_{12}COOH$). Oleic acid (CH3(CH2)7CH═CH (CH2)7COOH) is an example of a naturally occurring unsaturated fatty acid. It should be appreciated that compounds of the present approach involve Bedaquiline conjugated with a linear, saturated fatty acid, and preferably a linear, saturated fatty acid having from 3 to 20 carbon atoms, and more preferably from 7 to 19 carbon atoms, and even more preferably, from 12 to 16 carbon atoms in total. In demonstrative embodiments, the linear, saturated fatty acid is myristic acid, having 14 carbon atoms.

Bedaquiline and certain Bedaquiline derivatives having a fatty acid moiety may be used to selectively eradicate CSCs for treating and/or preventing tumor recurrence and/or metastasis. Bedaquiline is a drug presently used and FDA-approved to treat active tuberculosis, and in particular, multi-drug-resistant tuberculosis. Mechanistically, Bedaquiline blocks the proton pump for ATP synthase of mycobacteria. Cellular energy production is dependent upon ATP production, and the loss of ATP production results in an inhibition of mycobacterial growth.

As described herein, in vitro experiments show that Bedaquiline also targets the mitochondrial ATP synthase of malignant mammalian cells and reduce the rate of tumor recurrence and metastasis. Under the present approach, a pharmaceutically effective amount of Bedaquiline, or a Bedaquiline derivative having a fatty acid moiety as described herein, may be administered to a subject having cancer to treat and/or prevent tumor recurrence and/or metastasis. For example, in some embodiments for treating adult human subjects, 400 mg of Bedaquiline may be administered daily for 1 to 2 weeks, in tablet form, and then 600 mg of Bedaquiline may be administered 3 times per week for another 1 to 2 weeks, also in tablet form. This demonstrative dose is presently used for treating multi-drug-resistant tuberculosis in adults. The pharmaceutically effective amount of Bedaquiline used to treat and/or prevent tumor recurrence and/or metastasis, under the present approach, may vary, depending on the subject (e.g., age, weight, health conditions, etc.), as is known in the art. In embodiments of the present approach involving a Bedaquiline derivative having a fatty acid moiety, the pharmaceutically effective amount used to treat and/or prevent tumor recurrence and/or metastasis, under the present approach, will be lower than the pharmaceutically effective amount of Bedaquiline. The determination of a pharmaceutically effective amount is deemed to be within the purview of the person having an ordinary level of skill in the art, having reviewed this disclosure. It should be appreciated that the treatment cycle may be the same as or similar to the treatment cycle for treating tuberculosis, or may be different depending on the particular embodiment, the Bedaquiline derivative used, and other factors known in the art.

The inventors developed the present approach through first exploring the role of ATP synthesis in cancer cells, and then analyzing the impact of inhibiting ATP production in cancer cells. After identifying a target gene for ATP inhibition, the inventors evaluated various compounds for ATP inhibition activity, using various assays such as the mammosphere formation assay and the chick chorioallantoic membrane ("CAM") assay. The following paragraphs describe the bioinformatic analysis of the role of ATP synthesis. This discussion addresses the importance of ATP5F1C, the gamma-subunit of the mitochondrial ATP-synthase, in cancer metastasis. The ATP5F1C gene encodes a subunit of mitochondrial ATP synthase. Mitochondrial ATP synthase catalyzes ATP synthesis, using an electrochemical gradient of protons across the inner membrane during oxidative phosphorylation. The catalytic portion of mitochondrial ATP synthase consists of 5 different subunits (alpha, beta, gamma, delta, and epsilon). This gene encodes the gamma subunit of the catalytic core.

The inventors determined that mitochondrial ATP synthesis is a key determinant of 3D anchorage-independent growth and metastasis, using a bioinformatics approach. As a first step, GEO transcriptional profiling DataSets were analyzed to compare 2D-growth, 3D-growth, and the in vivo tumor growth of MDA-MB-231 cells, a triple-negative breast cancer (TNBC) cell line. HeatMaps were generated, highlighting that ATP-related genes were transcriptionally upregulated under both 3D growth conditions (anchorage-independent and in vivo tumors), all relative to 2D-adherent growth.

FIG. 1A shows a HeatMap comparing the transcriptional profiles of ATP-related genes (OXPHOS and ATP-related transporters), using the GSE36953 GEO DataSet, previously deposited in the NCBI database. HeatMaps are typically used in molecular biology to represent the level of expression of many genes across a number of comparable samples (e.g. cells in different states, samples from different patients) as they are obtained from DNA microarrays. HeatMaps are normally presented in color, with green shades indicating a negative log fold change ("FC") value, and red shades indicating a positive log FC value. The brighter the shade, the larger the log FC. Due to PCT Rule 11.13, FIG. 1A is presented in black and white. The color version of FIG. 1A shows green primarily in the first column, for 2D cells, and red shares in the second and third columns, for 3D and xenograft cells. In FIG. 1A, the lighter shades represent a higher absolute value of the log FC, noting that the 2D cells in the first column showed negative log FC. Total RNA was prepared from MDA-MB-231 cells, a TNBC cell line, under three different growth conditions: 2D-adherent growth, 3D-anchorage-independent growth and in vivo tumor growth. Analysis was performed with the Affymetrix Human Genome U133 Plus 2.0 Array. The HeatMap was generated with QIAGEN OmicSoft Suite Software. A $-4<\text{Log FC}>+4$ HeatMap scale bar is shown. Note that ATP-related genes were transcriptionally upregulated under both 3D growth conditions (anchorage-independent and in vivo tumors), all relative to 2D-adherent growth.

Figure 1B:
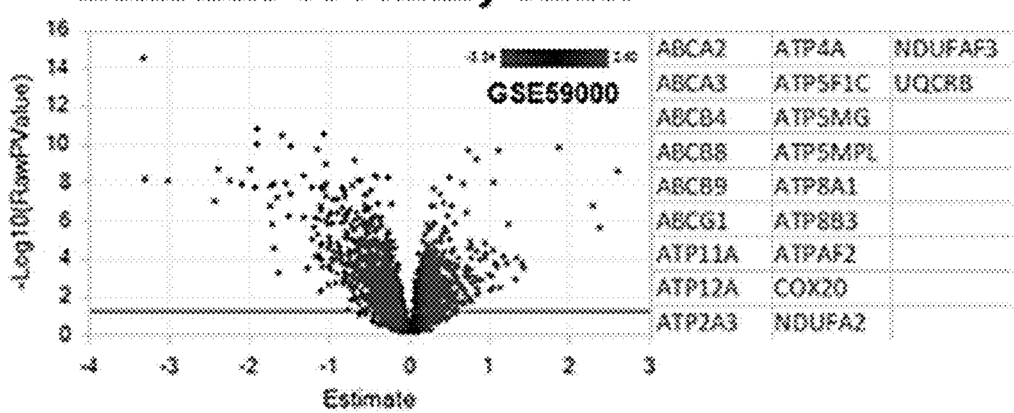
FIGS. 1B and 1C show volcano plots for the GSE2034 and GSE59000 GEO DataSets, respectively.
Figure 1C:
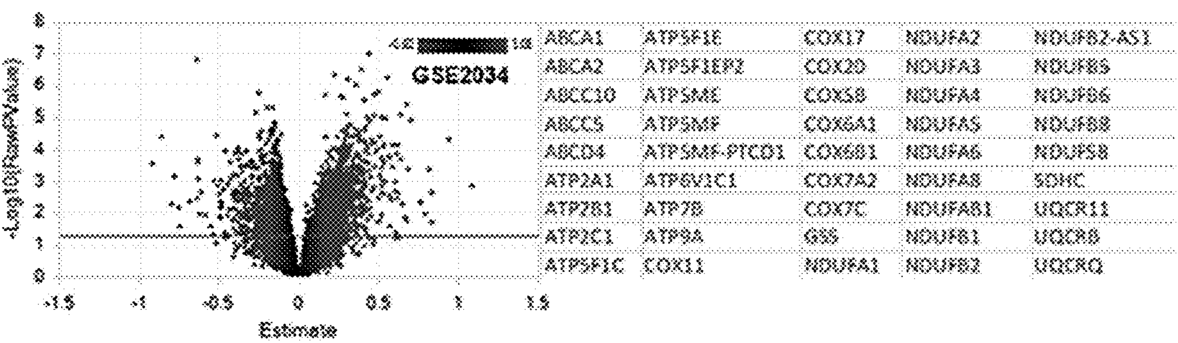

The transcriptional expression of ATP-related genes (OXPHOS and ATP-related transporters) were examined in two distinct GEO DataSets related to human breast cancer metastasis, revealing ATP-related genes that operate as biomarkers of metastasis. FIGS. 1B and 1C show volcano plots for the GSE2034 and GSE59000 GEO DataSets, respectively. These types of plots are normally in color, similar to the HeatMap discussed above. In black and white, the shares to the left of 0 represent green (indicating a negative correlation), and the shades to the right of 0 represent red (indicating a positive correlation). GSE2034 compares Breast Cancer Metastasis to No Breast Cancer Metastasis. GSE59000 compares Breast Cancer Metastasis to Breast Cancer Primary Tumor. These volcano plots were produced by examining the annotations present in OncoLand Metastatic Cancer (QIAGEN OmicSoft Suite) and by performing functional "core analyses" using Ingenuity Pathway Analysis Software (IPA; QIAGEN), on genes annotated with an uncorrected p-value cut off $<0.05$. Note that the transcriptional profiles of ATP-related genes (OXPHOS and ATP-related transporters), were increased and specifically associated with metastasis, in both GEO DataSets.

Figures 1D, 1E:
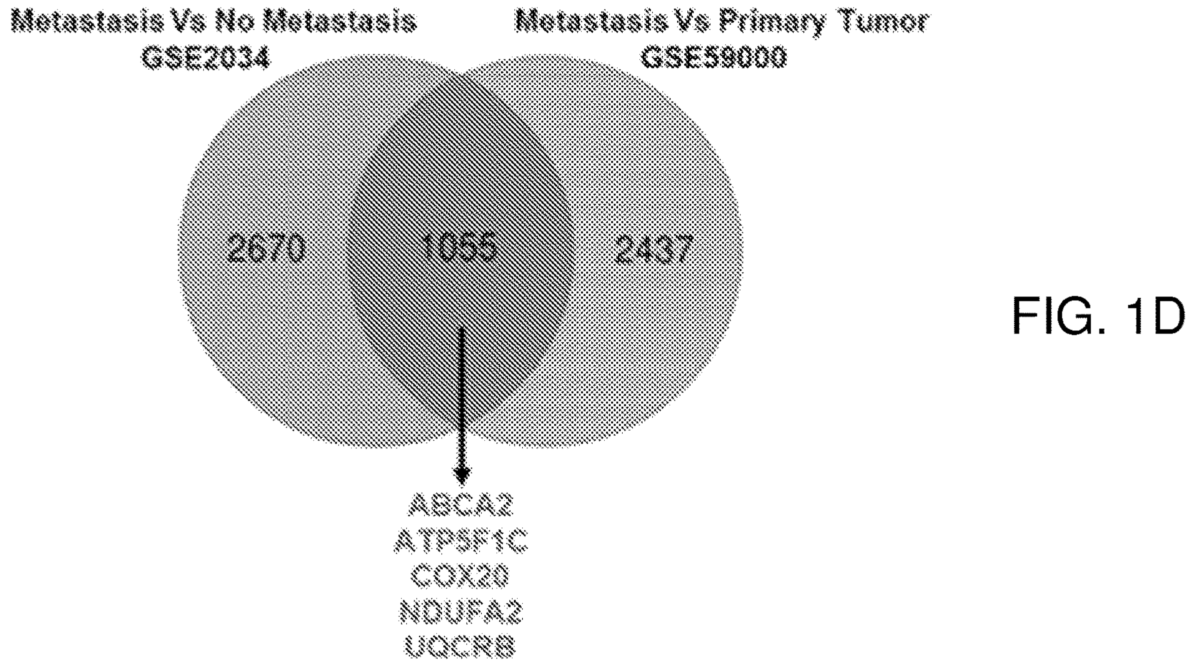
FIG. 1D is a Venn diagram showing the intersection of the two GEO DataSets.
FIG. 1E is a table of the genes correlated with ATP5F1C.

FIG. 1D is a Venn diagram showing the intersection of the two GEO DataSets, resulting in a five-member ATP-related metastasis gene-signature, consisting of ABCA2, ATP5F1C, COX20, NDUFA2 and UQCRB. FIG. 1E is a table of the genes correlated with ATP5F1C. Most notably, ATP5F1C (also known as ATP5C1) encodes the gamma-subunit of the soluble F1-catalytic core of the mitochondrial ATP synthase, complex V.

In bona fide breast cancer metastatic lesions, ATP5F1C transcriptional expression is positively correlated with the co-expression of: i) five metastatic marker genes (EPCAM, MKI67, RRP1B, VCAM1, CXCR4), ii) four cell cycle regulatory genes (CDK1, CDK2, CDK4, CDK6) and iii) eleven cancer stem cell (CSC) marker genes (CDH1, ALDH2, ALDHIBA1, ALDH9A1, SOX2, VIM, CDH2, ALDH7A1, ALDH1B1, CD44, ALDH3B2, listed in rank order of statistical significance). Tables 1-12 below present the expression data for various gene groups correlated with ATP5F1C. As can be seen, ATP5F1C transcriptional expression is also positively correlated with the co-expression of mitochondrial complexes I-V, mt-DNA encoded transcripts and three other members of the five-member metastasis gene-signature, namely UQCRB, COX20 and NDUFA2.

TABLE 1

Complex I gene transcripts correlated with ATP5F1C

| Correlated Gene | Cytoband | Spearman's Correlation | p-Value | q-Value |
|---|---|---|---|---|
| NDUFAB1 | 16p12.2 | 0.616 | 1.33E−16 | 6.10E−14 |
| NDUFA12 | 12q22 | 0.575 | 3.11E−14 | 5.88E−12 |
| NDUFA1 | Xq24 | 0.52 | 1.67E−11 | 1.44E−09 |
| NDUFA8 | 9q33.2 | 0.516 | 2.65E−11 | 2.08E−09 |
| NDUFAF4 | 6q16.1 | 0.511 | 4.54E−11 | 3.19E−09 |
| NDUFA6 | 22q13.2 | 0.505 | 8.33E−11 | 5.53E−09 |
| NDUFA9 | 12p13.32 | 0.457 | 6.73E−09 | 2.38E−07 |
| NDUFA3 | 19q13.42 | 0.418 | 1.51E−07 | 3.44E−06 |
| NDUFAF6 | 8q22.1 | 0.409 | 2.97E−07 | 6.10E−06 |
| NDUFA4 | 7p21.3 | 0.391 | 1.10E−06 | 1.87E−05 |
| NDUFA11 | 19p13.3 | 0.39 | 1.11E−06 | 1.89E−05 |
| NDUFA5 | 7q31.32 | 0.338 | 3.06E−05 | 3.21E−04 |
| NDUFAF2 | 5q12.1 | 0.287 | 4.49E−04 | 3.06E−03 |
| NDUFA13 | 19p13.11 | 0.276 | 7.45E−04 | 4.69E−03 |
| NDUFAF5 | 20p12.1 | 0.255 | 1.93E−03 | 0.0104 |
| NDUFAF3 | 3p21.31 | 0.236 | 4.21E−03 | 0.0199 |
| NDUFA10 | 2q37.3 | 0.197 | 0.0171 | 0.0606 |
| NDUFA4L2 | 12q13.3 | 0.19 | 0.0218 | 0.0732 |
| NDUFA2 | 5q31.3 | 0.181 | 0.0286 | 0.0905 |
| NDUFAF7 | 2p22.2 | 0.179 | 0.0304 | 0.0947 |

TABLE 2

Complex II gene transcripts correlated with ATP5F1C

| Correlated Gene | Cytoband | Spearman's Correlation | p-Value | q-Value |
|---|---|---|---|---|
| SDHD | 11q23.1 | 0.427 | 7.82E−08 | 1.94E−06 |
| SDHAF3 | 7q21.3 | 0.424 | 9.51E−08 | 2.31E−06 |
| SDHA | 5p15.33 | 0.416 | 1.75E−07 | 3.92E−06 |
| SDHC | 1q23.3 | 0.413 | 2.26E−07 | 4.86E−06 |
| SDHB | 1p36.13 | 0.398 | 6.73E−07 | 1.24E−05 |
| SDHAF4 | 6q13 | 0.357 | 9.61E−06 | 1.19E−04 |
| SDHAF2 | 11q12.2 | 0.2 | 0.0157 | 0.0568 |

TABLE 3

Complex III gene transcripts correlated with ATP5F1C

| Correlated Gene | Cytoband | Spearman's Correlation | p-Value | q-Value |
|---|---|---|---|---|
| UQCRF51 | 19q12 | 0.58 | 1.61E−14 | 3.41E−12 |
| UQCR10 | 22q12.2 | 0.553 | 4.61E−13 | 6.14E−11 |
| UQCRH | 1p33 | 0.518 | 2.07E−11 | 1.69E−09 |
| UQCRHL | 1p36.21 | 0.518 | 2.07E−11 | 1.69E−09 |
| UQCRB | 8q22.1 | 0.457 | 6.89E−09 | 2.43E−07 |
| UQCRC2 | 16p12.2 | 0.393 | 9.30E−07 | 1.64E−05 |
| UQCRC1 | 3p21.31 | 0.371 | 3.91E−06 | 5.61E−05 |
| UQCRQ | 5q31.1 | 0.335 | 3.60E−05 | 3.69E−04 |
| UQCR11 | 19p13.3 | 0.322 | 7.45E−05 | 6.81E−04 |

TABLE 4

Complex IV gene transcripts correlated with ATP5F1C

| Correlated Gene | Cytoband | Spearman's Correlation | p-Value | q-Value |
|---|---|---|---|---|
| COX7B | Xq21.2 | 0.591 | 4.34E−15 | 1.12E−12 |
| COX6B1 | 19q13.12 | 0.562 | 1.53E−13 | 2.36E−11 |
| COX5A | 15q24.2 | 0.555 | 3.52E−13 | 4.83E−11 |
| COX7A2 | 6q14.1 | 0.517 | 2.42E−11 | 1.95E−09 |

TABLE 4-continued

Complex IV gene transcripts correlated with ATP5F1C

| Correlated Gene | Cytoband | Spearman's Correlation | p-Value | q-Value |
|---|---|---|---|---|
| COX5B | 2q11.2 | 0.505 | 8.73E−11 | 5.76E−09 |
| COX4I1 | 16q24.1 | 0.499 | 1.46E−10 | 8.96E−09 |
| COX6A1 | 12q24.31\|12q24.2 | 0.482 | 7.29E−10 | 3.52E−08 |
| COX8A | 11q13.1 | 0.466 | 3.20E−09 | 1.25E−07 |
| COX7C | 5q14.3 | 0.439 | 2.93E−08 | 8.32E−07 |
| COX16 | 14q24.2 | 0.401 | 5.23E−07 | 9.99E−06 |
| COX17 | 3q13.33 | 0.36 | 8.12E−06 | 1.04E−04 |
| COX7A2L | 2p21 | 0.326 | 5.87E−05 | 5.60E−04 |
| COX14 | 12q13.12 | 0.308 | 1.52E−04 | 1.23E−03 |
| COX19 | 7p22.3 | 0.302 | 2.10E−04 | 1.62E−03 |
| COX18 | 4q13.3 | 0.257 | 1.73E−03 | 9.54E−03 |
| ACOX1 | 17q25.1 | 0.255 | 1.86E−03 | 0.0101 |
| COX20 | 1q44 | 0.232 | 4.78E−03 | 0.022 |
| COX15 | 10q24.2 | 0.198 | 0.0163 | 0.0585 |
| COX6C | 8q22.2 | 0.196 | 0.018 | 0.0632 |
| COX7B2 | 4p12 | 0.192 | 0.0201 | 0.0686 |
| COX6A2 | 16p11.2 | 0.18 | 0.0298 | 0.0935 |
| COX7A1 | 19q13.12 | 0.177 | 0.0324 | 0.0997 |

TABLE 5

Complex 5 gene transcripts correlated with ATP5F1C

| Correlated Gene | Cytoband | Spearman's Correlation | p-Value | q-Value |
|---|---|---|---|---|
| ATP5MF | 7q22.1 | 0.687 | 1.08E−21 | 4.85E−18 |
| ATP5MC3 | 2q31.1 | 0.624 | 4.10E−17 | 2.49E−14 |
| ATP5MD | 10q24.33 | 0.612 | 2.25E−16 | 9.37E−14 |
| ATP5PB | 1p13.2 | 0.605 | 6.09E−16 | 2.19E−13 |
| ATP5MG | 11q23.3 | 0.585 | 9.25E−15 | 2.12E−12 |
| ATP5F1B | 12q13.3 | 0.579 | 1.92E−14 | 3.93E−12 |
| ATP5PO | 21q22.11 | 0.578 | 2.24E−14 | 4.42E−12 |
| ATP5F1E | 20q13.22 | 0.535 | 3.58E−12 | 3.82E−10 |
| ATP5PD | 17q25.1 | 0.532 | 4.99E−12 | 5.15E−10 |
| ATP5F1A | 18q21.1 | 0.516 | 2.67E−11 | 2.08E−09 |
| ATP5MPL | 14q32.33 | 0.512 | 3.84E−11 | 2.78E−09 |
| ATP5PF | 21q21.3 | 0.503 | 9.53E−11 | 6.25E−09 |
| ATP5ME | 4p16.3 | 0.486 | 5.02E−10 | 2.53E−08 |
| ATP5IF1 | 1p35.3 | 0.357 | 9.53E−06 | 1.18E−04 |
| ATP5MC2 | 12q13.13 | 0.327 | 5.69E−05 | 5.47E−04 |
| ATP5MC1 | 17q21.32 | 0.285 | 4.82E−04 | 3.26E−03 |
| ATP5F1D | 19p13.3 | 0.264 | 1.31E−03 | 7.54E−03 |

TABLE 6

All ATP gene transcripts correlated with ATP5F1C

| Correlated Gene | Cytoband | Spearman's Correlation | p-Value | q-Value |
|---|---|---|---|---|
| ATP5MF | 7q22.1 | 0.687 | 1.08E−21 | 4.85E−18 |
| ATP5MC3 | 2q31.1 | 0.624 | 4.10E−17 | 2.49E−14 |
| ATP5MD | 10q24.33 | 0.612 | 2.25E−16 | 9.37E−14 |
| ATP5PB | 1p13.2 | 0.605 | 6.09E−16 | 2.19E−13 |
| ATP5MG | 11q23.3 | 0.585 | 9.25E−15 | 2.12E−12 |
| ATP5F1B | 12q13.3 | 0.579 | 1.92E−14 | 3.93E−12 |
| ATP5PO | 21q22.11 | 0.578 | 2.24E−14 | 4.42E−12 |
| ATP6V1A | 3q13.31 | 0.566 | 1.00E−13 | 3.62E−11 |
| ATP5F1E | 20q13.32 | 0.535 | 3.58E−12 | 3.82E−10 |
| ATP5PD | 17q23.1 | 0.532 | 4.99E−12 | 5.15E−10 |
| ATP6V1F | 7q32.1 | 0.528 | 7.71E−12 | 7.51E−10 |
| ATP5F1A | 18q21.1 | 0.516 | 2.67E−11 | 2.08E−09 |
| ATP5MPL | 14q32.22 | 0.512 | 3.84E−11 | 2.78E−09 |
| ATP5PF | 21q21.3 | 0.503 | 9.53E−11 | 1.25E−09 |
| ATP6V1E1 | 22q11.21 | 0.495 | 2.12E−10 | 1.24E−08 |
| ATP2A2 | 12q24.11 | 0.491 | 3.19E−10 | 1.75E−08 |
| ATP5ME | 4p16.3 | 0.486 | 5.02E−10 | 2.53E−08 |
| ATP6V1D | 14q23.3 | 0.43 | 5.95E−08 | 1.53E−08 |
| ATP6V0E1 | 5q35.1 | 0.424 | 9.80E−08 | 2.36E−06 |

TABLE 6-continued

All ATP gene transcripts correlated with ATP5F1C

| Correlated Gene | Cytoband | Spearman's Correlation | p-Value | q-Value |
|---|---|---|---|---|
| ATP1B3 | 3q23 | 0.422 | 1.14E−07 | 2.69E−06 |
| ATP6V1B2 | 8p21.3 | 0.407 | 3.34E−07 | 6.77E−06 |
| ATP11C | Xq27.1 | 0.405 | 4.08E−07 | 8.06E−06 |
| ATP6V1C1 | 8q22.3 | 0.404 | 4.24E−07 | 8.34E−06 |
| ATP6AP2 | Xp11.4 | 0.4 | 5.79E−07 | 1.09E−05 |
| ATP6V0C | 16p13.3 | 0.4 | 5.80E−07 | 1.09E−05 |
| ATP2C1 | 3q22.1 | 0.395 | 8.16E−07 | 1.46E−05 |
| ATP0V1H | 8q11.21 | 0.381 | 2.08E−06 | 3.28E−05 |
| ATP11B | 3q26.33 | 0.378 | 2.60E−06 | 3.94E−05 |
| ATP6V1G1 | 9q32 | 0.17 | 4.34E−06 | 6.16E−05 |
| ATP23 | 12q14.1 | 0.365 | 6.04E−06 | 8.12E−05 |
| ATP6AP1 | Xq28 | 0.358 | 8.98E−06 | 1.13E−04 |
| ATP5IF1 | 1p35.3 | 0.357 | 9.53E−06 | 1.18E−04 |
| ATP6V0B | 1p34.1 | 0.348 | 1.00E−05 | 1.91E−04 |
| ATP6V1E2 | 2p21\|2p16-p12 | 0.345 | 1.99E−05 | 2.20E−04 |
| ATP6V0A4 | 7q34 | 0.34 | 2.75E−05 | 2.94E−04 |
| ATP5MC2 | 12q13.13 | 0.327 | 5.69E−05 | 5.47E−04 |
| ATPAF1 | 1p33 | 0.313 | 1.20E−04 | 1.01E−03 |
| ATP6V0D1 | 16q22.1 | 0.306 | 1.72E−04 | 1.36E−03 |
| ATP2B1 | 12q21.33 | 0.305 | 1.85E−04 | 1.45E−03 |
| ATP6V0E2 | 7q36.1 | 0.3 | 2.39E−04 | 1.79E−03 |
| MT-ATP8 | — | 0.297 | 2.75E−04 | 2.03E−03 |
| ATP5MC1 | 17q21.32 | 0.285 | 4.82E−04 | 3.26E−03 |
| MT-ATP6 | — | 0.279 | 6.37E−04 | 4.10E−03 |
| ATP6V0A2 | 12q24.31 | 0.271 | 9.20E−04 | 5.60E−03 |
| ATP1A1 | 1p13.3 | 0.269 | 1.01E−03 | 6.09E−03 |
| ATP5F1D | 19p13.3 | 0.264 | 1.31E−03 | 7.54E−03 |
| ATP8A2 | 13q12.13 | 0.261 | 1.46E−03 | 8.28E−03 |
| ATP6V1C2 | — | 0.248 | 2.53E−03 | 0.0129 |
| ATP13A3 | 3q29 | 0.242 | 3.21E−03 | 0.0158 |
| ATP11A | 13q14 | 0.208 | 0.0119 | 0.0457 |
| ATP6V1G2 | 6p21.33 | 0.207 | 0.012 | 0.046 |

TABLE 7 mt-DNA gene transcripts correlated with ATP5F1C

| Correlated Gene | Cytoband | Spearman's Correlation | p-Value | q-Value |
|---|---|---|---|---|
| MT-RNR2 | — | 0.354 | 1.17E−05 | 1.41E−04 |
| MT-ND4 | — | 0.326 | 5.81E−05 | 5.55E−04 |
| MT-ND5 | — | 0.302 | 2.16E−04 | 1.65E−03 |
| MT-CO1 | — | 0.299 | 2.42E−04 | 1.82E−03 |
| MT-ATP8 | — | 0.297 | 2.75E−04 | 2.03E−03 |
| MT-ND1 | — | 0.291 | 3.67E−04 | 2.58E−03 |
| MT-CO3 | — | 0.289 | 4.10E−04 | 2.83E−03 |
| MT-ND3 | — | 0.286 | 4.62E−04 | 3.14E−03 |
| MT-ND2 | — | 0.285 | 4.89E−04 | 3.30E−03 |
| MT-CO2 | — | 0.282 | 5.72E−04 | 3.76E−03 |
| MT-ATP6 | — | 0.279 | 6.37E−04 | 4.10E−03 |
| MT-CY8 | — | 0.279 | 5.68E−04 | 4.22E−03 |
| MT-ND6 | — | 0.259 | 1.57E−03 | 8.78E−03 |
| MT-ND4L | — | 0.223 | 6.90E−03 | 0.0296 |

TABLE 8

ABC gene transcripts correlated with ATP5F1C

| Correlated Gene | Cytoband | Spearman's Correlation | p-Value | q-Value |
|---|---|---|---|---|
| ABCE1 | 4q31.21 | 0.478 | 1.03E−09 | 4.81E−08 |
| ABCF1 | 6p21.33 | 0.355 | 1.10E−05 | 1.34E−04 |
| ABCF2 | 7q36.1 | 0.274 | 8.22E−04 | 5.09E−03 |
| ABCC6P1 | 16p12.3 | 0.274 | 8.33E−04 | 5.14E−03 |
| ABCD3 | 1p21.3 | 0.269 | 1.04E−03 | 6.20E−03 |
| ABCB6 | 2q35 | 0.258 | 1.68E−03 | 9.32E−03 |
| ABCC2 | 10q24.2 | 0.232 | 4.82E−03 | 0.0222 |
| ABCC4 | 13q32.1 | 0.226 | 6.09E−03 | 0.0268 |

TABLE 8-continued

ABC gene transcripts correlated with ATP5F1C

| Correlated Gene | Cytoband | Spearman's Correlation | p-Value | q-Value |
|---|---|---|---|---|
| ABCC9 | 12p12.1 | 0.187 | 0.0236 | 0.0779 |
| ABCC6P2 | 16p13.11 | 0.186 | 0.0243 | 0.0759 |
| ABCG8 | 2p21 | 0.176 | 0.0334 | 0.102 |
| ABCD1 | Xq28 | 0.176 | 0.0334 | 0.102 |

TABLE 9

Breast cancer stem cell marker gene transcripts correlated with ATP5F1C

| Correlated Gene | Cytoband | Spearman's Correlation | p-Value | q-Value |
|---|---|---|---|---|
| CDH1 | 16q22.1 | 0.318 | 8.97E−05 | 7.93E−04 |
| ALDH2 | 12q24.12 | 0.315 | 1.10E−04 | 9.41E−04 |
| ALDH18A1 | 10q24.1 | 0.3 | 2.32E−04 | 1.75E−03 |
| ALDH9A1 | 1q24.1 | 0.262 | 1.40E−03 | 7.98E−03 |
| SOX2 | 3q26.33 | 0.256 | 1.78E−03 | 9.76E−03 |
| VIM | 10p13 | 0.255 | 1.93E−03 | 0.0104 |
| CDH2 | 18q12.1 | 0.249 | 2.41E−03 | 1.25E−02 |
| ALDH7A1 | 5q23.2 | 0.244 | 3.02E−03 | 1.50E−02 |
| ALDH1B1 | 9p13.1 | 0.235 | 4.33E−03 | 0.0203 |
| CD44 | 11p13 | 0.229 | 5.51E−03 | 2.47E−02 |
| ALDH3B2 | 11q13.2 | 0.227 | 5.97E−03 | 0.0264 |

TABLE 10

Metastatic marker gene transcripts correlated with ATP5F1C

| Correlated Gene | Cytoband | Spearman's Correlation | p-Value | q-Value |
|---|---|---|---|---|
| EPCAM | 2p21 | 0.578 | 2.29E−14 | 4.47E−12 |
| MKI67 | 10q26.2 | 0.359 | 8.42E−06 | 1.07E−04 |
| RRP1B | 21q22.3 | 0.346 | 1.88E−05 | 2.12E−04 |
| VCAM1 | 1p21.2 | 0.304 | 1.91E−04 | 1.49E−03 |
| CXCR4 | 2q22.1 | 0.295 | 2.96E−04 | 2.15E−03 |

TABLE 11

Cell cycle gene transcripts correlated with ATP5F1C

| Correlated Gene | Cytoband | Spearman's Correlation | p-Value | q-Value |
|---|---|---|---|---|
| CDK1 | 10q21.2 | 0.436 | 3.84E−08 | 1.05E−06 |
| CDK2 | 12q13.2 | 0.224 | 6.51E−03 | 2.82E−02 |
| CDK4 | 12q14.1 | 0.306 | 1.74E−04 | 1.37E−03 |
| CDK6 | 7q21.2 | 0.292 | 3.47E−04 | 2.46E−03 |

Similarly, the expression of two members of this metastasis gene signature, namely ATP5F1C and UQCRB, have been functionally correlated with maximal oxygen uptake ($VO_{2max}$) and a high percentage of type 1 fibers (mitochondrial-rich) in human skeletal muscle tissues. The expression of ATP5F1C in skeletal muscle is also increased significantly after exercise training, reflecting increased muscle fitness in patients. Conversely, ATP5F1C levels decreased with advanced age and were reduced in progeria syndrome patients. These results are highly suggestive that high ATP5F1C expression is a biomarker of increased mitochondrial ATP production at the cellular level.

Figure 2A:
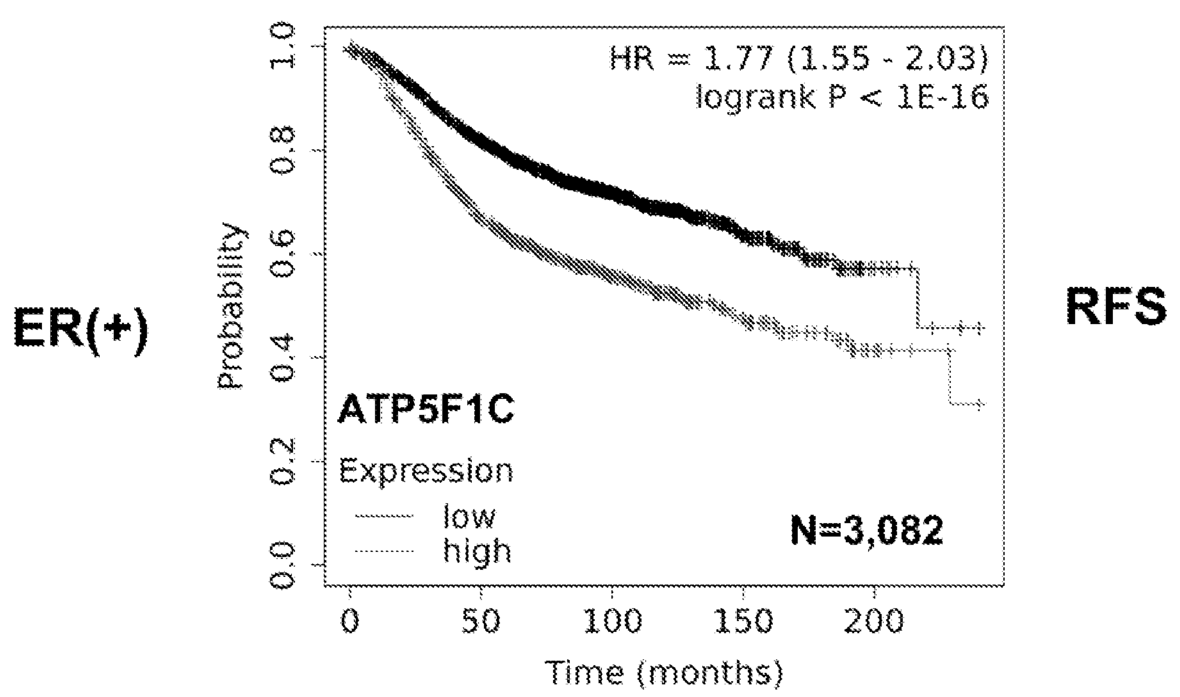
FIGS. 2A-2C are KM plots for ER(+) relapse-free survival ("RFS"), ER(+) distant metastasis-free survival ("DMFS"), and ER(+) LN-negative, Tamoxifen-treated RFS, respectively.
Figure 2B:
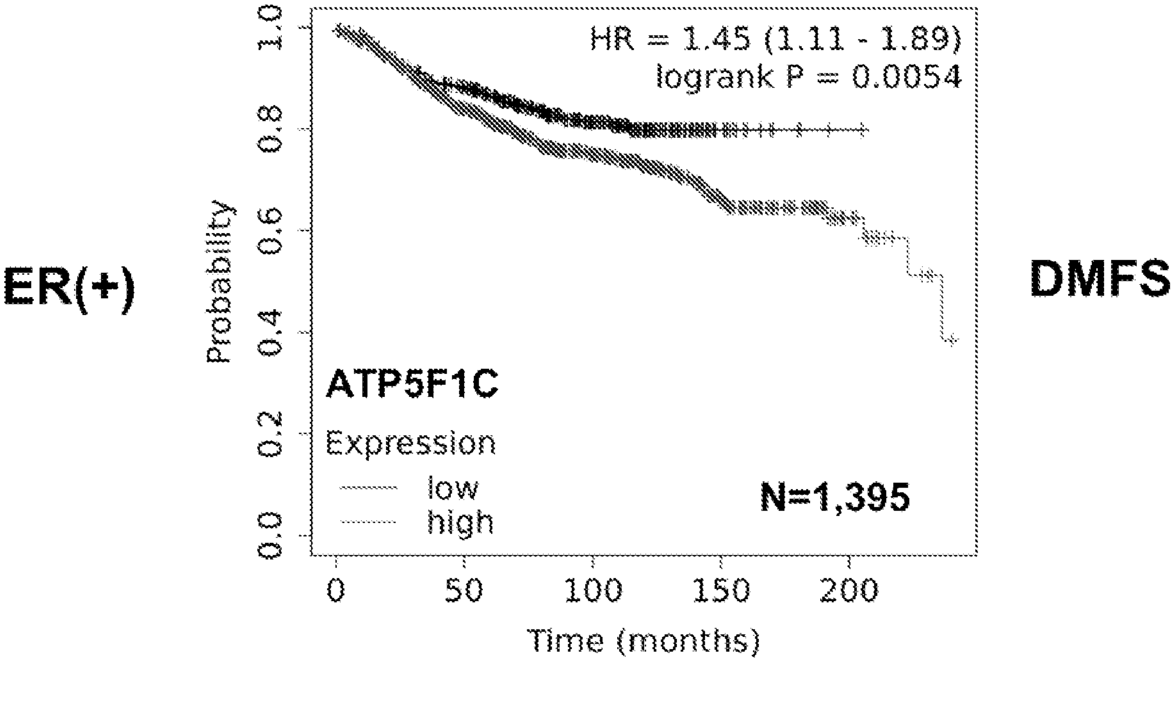
Figure 2C:
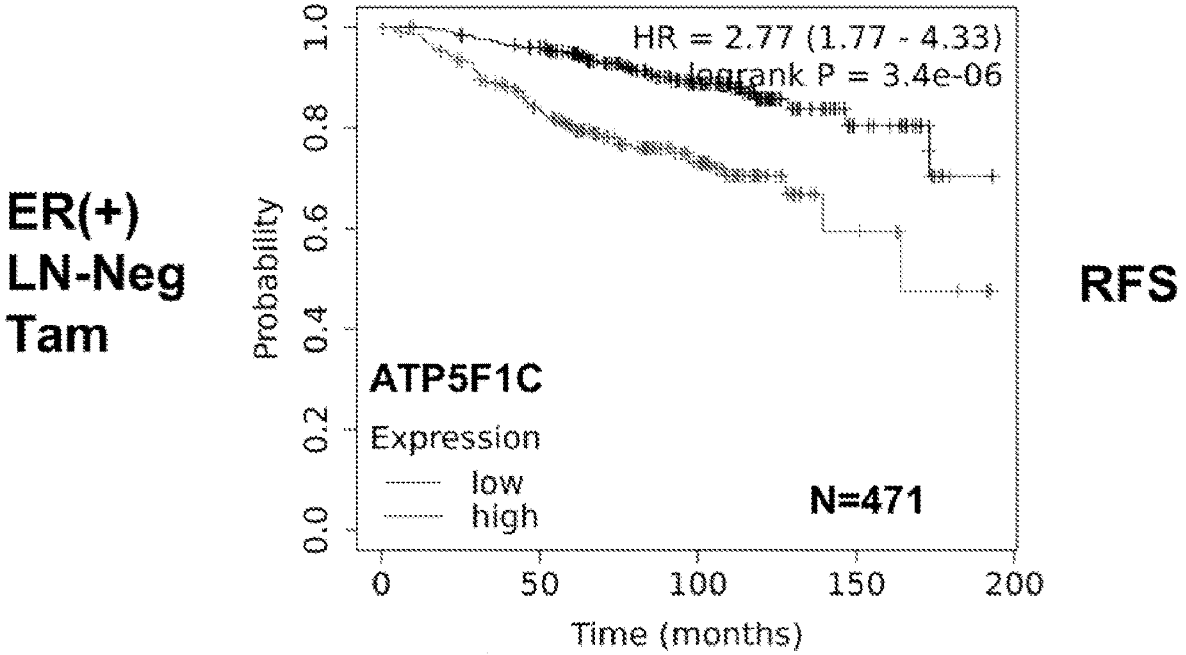

Using Kaplan-Meier (K-M) analysis, ATP5F1C was determined to be a prognostic biomarker for distant metastasis and tumor recurrence, especially in ER(+) patients that are lymph node negative at diagnosis and were treated with Tamoxifen (HR (RFS)=2.77; P=3.4E=06; N=471). FIGS. 2A-2C are KM plots for ER(+) relapse-free survival ("RFS"), ER(+) distant metastasis-free survival ("DMFS"), and ER(+) LN-negative, Tamoxifen-treated RFS, respectively. Hazard ratios ("HR") are shown on the drawings. To perform K-M analysis on ATP5F1C, an open-access online survival analysis tool was used to interrogate publicly-available microarray data from breast cancer patients. This approach allowed for a direct in silico validation of ATP5F1C as a marker of tumor recurrence.

In addition, the inventors determined that ATP-related genes and OXPHOS genes are transcriptional biomarkers of breast cancer circulating tumor cells (CTCs) in patients, using existing GEO DataSets. HeatMaps of ATP-ABC and OXPHOS genes from GSE55470 were used to determine that high ATP content in CTCs may be useful as a biomarker, to identify and track CTCs in whole blood, thereby potentially improving cancer diagnosis and preventing metastatic spread.

Figure 3:
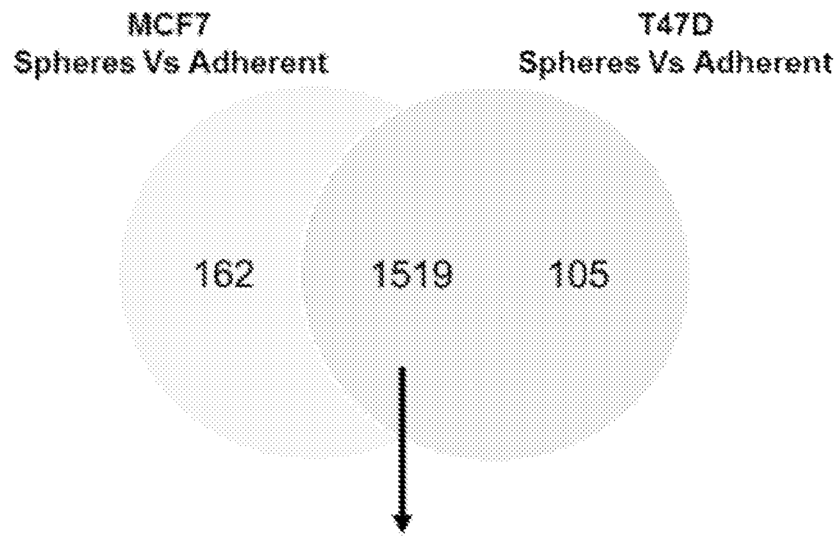
FIG. 3 shows a Venn diagram of proteins in MCF7 and T47D data sets, and includes a table of up-regulated ATP-related proteins in each data set.

The inventors also re-interrogated existing proteomic profiling data, comparing 2D-monolayers with 3D-mammospheres, in two distinct ER(+) breast cancer cell lines, namely MCF7 and T47D. Overall, from 1,519 common proteins in both cell lines, 21 ATP-related proteins were found to be up-regulated in both data sets, in 3D-mammospheres. FIG. 3 shows a Venn diagram of proteins in both data sets, and includes a table of up-regulated ATP-related proteins in each data set. Out of these 21 ATP-related proteins, 7 subunits of the mitochondrial ATP-synthase were detected, including ATP5F1B, ATP5F1C, ATP5IF1, ATP5MG, ATP5PB, ATP5PD and ATP5PO. FIG. 3 is a Venn diagram comparing the proteomic profiles of two ER(+) breast cancer cell lines (MCF7 and T47D) were first compared, under 2D-adherent and 3D-anchorage-independent growth conditions. Commonly shared ATP-related gene products (OXPHOS and ATP-related transporters) are enumerated below the Venn diagram. From 1519 common proteins, 21 ATP-related proteins were found to be upregulated in both data sets. Proteomic data sets were interrogated by performing functional "core analyses" using Ingenuity Pathway Analysis Software (IPA; QIAGEN).

Taken together, the bioinformatic analysis confirms that increased mitochondrial ATP synthesis could be a key driver of 3D anchorage-independent growth and metastasis. Consistent with confirmation, the inventors determined that shRNA-targeted knock-down of ATP5F1C protein expression inhibits ATP production, cell migration and 3D anchorage-independent growth.

Figure 4:
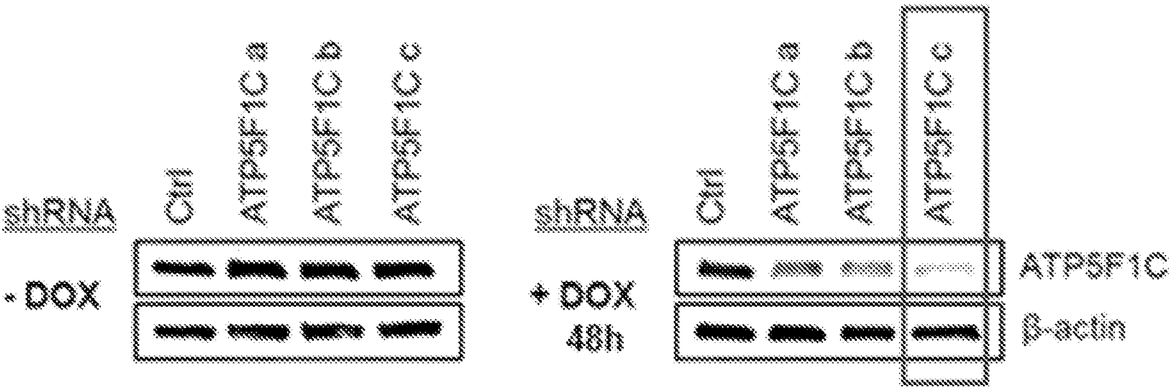
FIG. 4 shows a Western blot analysis of MDA-MB-231 cells stably-transduced with a lenti-viral vector encoding an shRNA targeting ATP5F1C, in the Tet-On system.

The inventors identified ATP5F1C as a clinical biomarker of cancer metastasis. In order to further validate its functional relevance as a potential therapeutic target, an shRNA approach was used to down-regulate ATP5F1C expression in an inducible manner, by employing the Tet-On system, engineered into a single lentiviral vector. FIG. 4 is a Western blot analysis of MDA-MB-231 cells stably-transduced with a *lenti*-viral vector encoding an shRNA targeting ATP5F1C, in the Tet-On system. Three different shRNA constructs (a, b, and c) were tested. MDA-MB-231 cells were also transduced with an shRNA-control vector in parallel. After 48 hours of shRNA-induction by treatment with Doxycycline (10 μM), the levels of ATP5F1C were assessed by Western blot analysis. Note that only the shRNA construct c showed inducible down-regulation of ATP5F1C expression levels, as indicated by the light gray box around the results for +DOX. As a consequence, only cells transduced with construct c were used for further experiments, as compared with the shRNA control.

FIG. 4 shows that, using this approach, ATP5F1C expression is successfully down-regulated in an inducible manner, by using low levels of Doxycycline. Importantly, by using this genetic approach to ablate ATP5F1C expression, loss of ATP5F1C is shown to be sufficient to phenotypically inhibit i) ATP production, ii) cell migration and iii) 3D anchorage-independent growth.

Figure 5A:
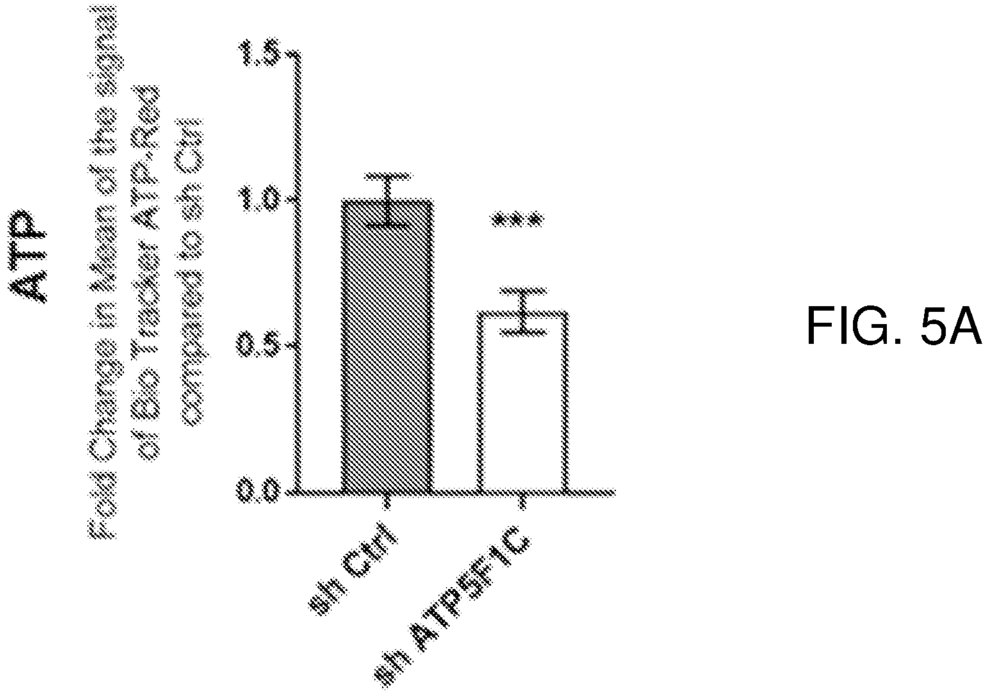
FIGS. 5A-5D show the results of ATP5F1C knock-down on ATP production, cell migration, and 3D anchorage-independent growth.
Figure 5B:
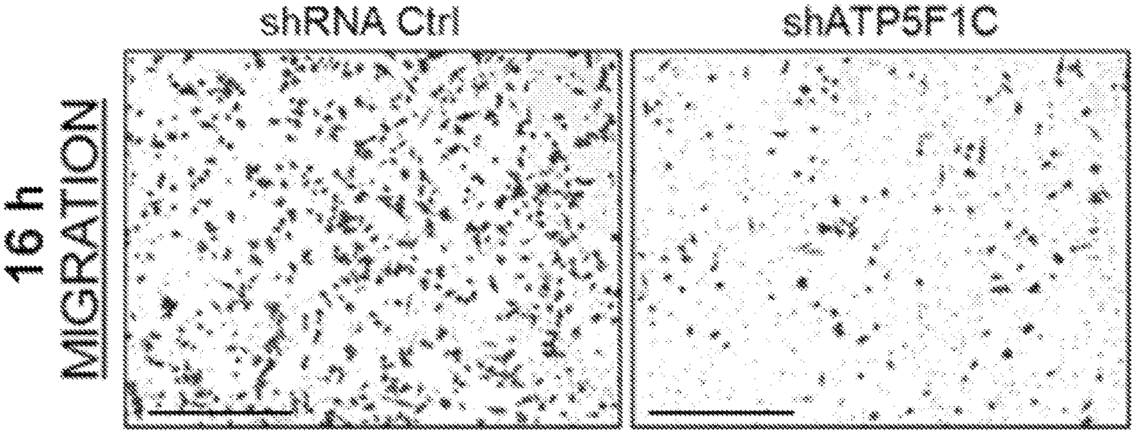
Figure 5C:
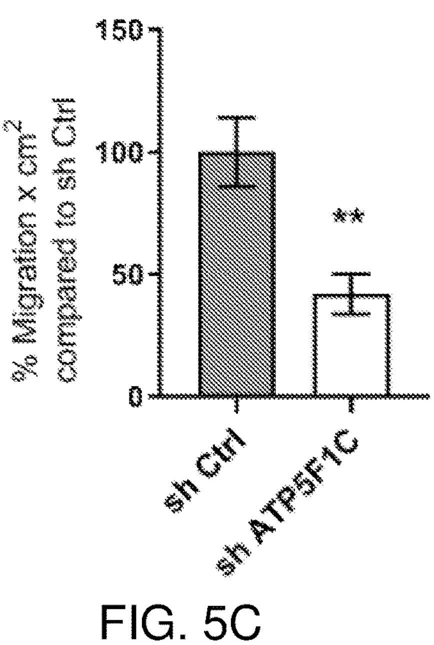
Figure 5D:
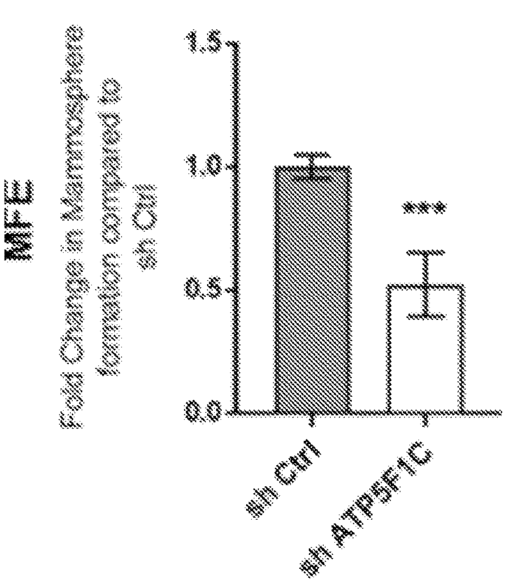

FIGS. 5A-5D show the results of ATP5F1C known-down on ATP production, cell migration, and 3D anchorage-independent growth. First, FIG. 5A compares the fold-change of BioTracker ATP-Red (signal mean) between the control and the ATP5F1C known-down. Induced down-regulation of ATP5F1C reduces ATP levels by ~45%, relative to the shRNA control. Unpaired t-test, p<0.005. FIG. 5B shows representative images of cell migration after 16 hours, for both the control and the ATP5F1C knock-down. FIG. 5C presents the data as a percentage of the control. As can be seen, induced down-regulation of ATP5F1C blocks cell migration by ~65%, relative to the shRNA control. MDA-MB-231 cells were cultured in presence of Doxycycline (10 μM) for 32 hours and moved to the Transwells for 16 hours, in presence of Doxycycline. Unpaired t-test, p<0.005. FIG. 5D shows results of the mammosphere formation assay. As can be seen, knock-down of ATP5F1C inhibits 3D anchorage-independent growth. Induced down-regulation of ATP5F1C blocks 3D mammosphere formation by ~50%, relative to the shRNA control. Unpaired t-test, ***p<0.0005.

The data demonstrates that ATP5F1C is a suitable target for treating tumor recurrence and metastasis. The inventors determined that targeting ATP5F1C with either Bedaquiline or certain conjugates of Bedaquiline, prevents ATP production, cell migration, 3D anchorage-independent growth, and metastasis in vivo. Bedaquiline (structure [1], below) is an FDA-approved antibiotic that is reserved for the treatment of multi-drug resistant tuberculosis (TB). It is further described in U.S. Pat. No. 7,498,343, issued Mar. 3, 2009, and in U.S. Pat. No. 8,546,428, issued Oct. 1, 2013, both of which are incorporated by reference in their entirety. Chemically, Bedaquiline mechanistically inhibits the myco-bacterial ATP-synthase. However, the studies described herein highlight that Bedaquiline also specifically binds to the human mitochondrial ATP-synthase and potently inhibits its activity. Ultrastructurally, detailed cryo-EM studies have shown that the binding site of Bedaquiline includes direct contact with the C-ring (ATP5G1/2/3), which is in close contact with the gamma subunit of the mitochondrial ATP-synthase, namely ATP5F1C.

[1]

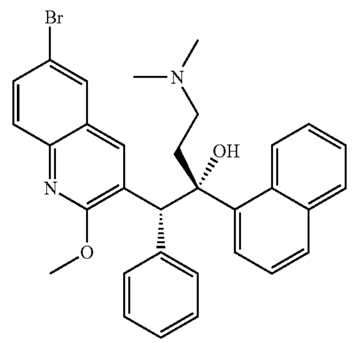

Figure 6:
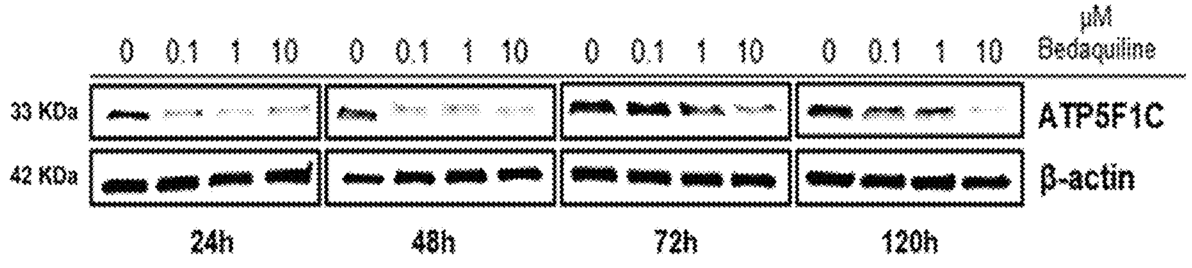
FIG. 6 shows a Western blot analysis of MDA-MB-231 2D cell monolayers treated with varying concentrations of Bedaquiline, over time.

The binding of Bedaquiline to ATP5F1C in situ induces degradation of the protein. FIG. 6 shows a Western blot analysis of MDA-MB-231 2D cell monolayers treated with Bedaquiline (at 0, 0.1, 1 and 10 μM), at 4 time points (24, 48, 72 and 120 hours of incubation). Note that the levels of ATP5F1C protein expression were reduced in a sustained way, especially at 10 μM Bedaquiline, relative to vehicle-alone (DMSO) controls. The results show that the expression of ATP5F1C was down-regulated in response to Bedaquiline treatment. The effect was both time- and concentration-dependent.

Figure 7:
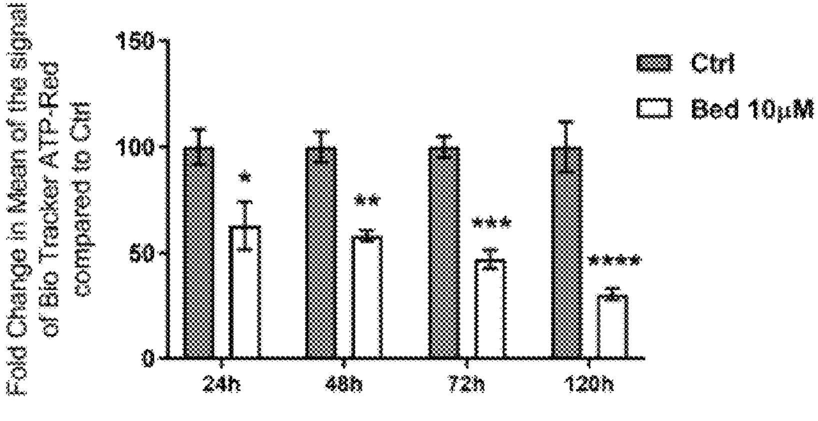
FIG. 7 compares the fold-change of BioTracker ATP-Red (signal mean) between the control and MDA-MB-231 cells treated with Bedaquiline.

Further, loss of ATP5F1C expression induced by Bedaquiline-treatment resulted in mitochondrial ATP-depletion, by up to 75%. FIG. 7 compares the fold-change of BioTracker ATP-Red (signal mean) between the control and MDA-MB-231 cells treated with Bedaquiline. As can be seen, Bedaquiline reduces mitochondrial ATP production. Note that Bedaquiline significantly inhibited mitochondrial ATP production in MDA-MB-231 cells, at a concentration of 10 μM, in a time-dependent manner, as assessed using BioTracker ATP-Red 1, to specifically detect mitochondrial ATP levels. Maximal inhibition of 75% was observed at 120 hours of treatment. The data in FIG. 7 based on two-way ANOVA, Sidak's multiple comparisons test, *$p<0.05$, $p<0.005$, *$p<0.0005$, ****$p<0.0001$.

Figure 8A:
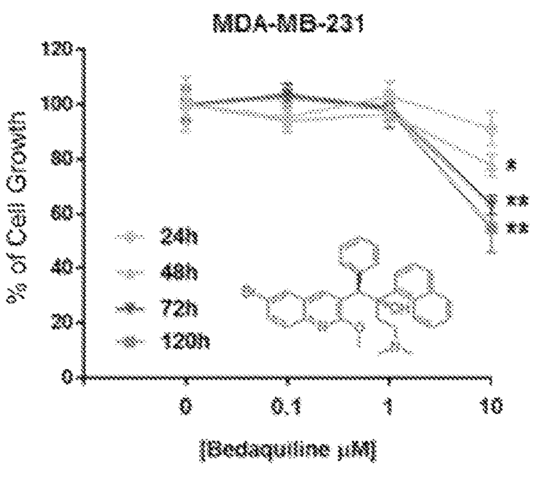
FIGS. 8A and 8B show monolayer growth of MDA-MB-231 and MCF10A cells, respectively, treated with 10 μM Bedaquiline over time.
Figure 8B:
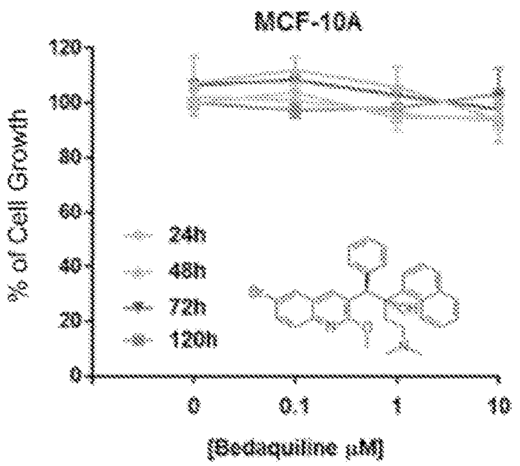

ATP-depletion induced by Bedaquiline also inhibited the growth of MDA-MB-231 cells in 2D monolayers, but did not affect the growth of MCF10A cells, a non-tumorigenic human breast epithelial cell line. FIGS. 8A and 8B show monolayer growth of MDA-MB-231 and MCF10A cells, respectively, treated with 10 μM Bedaquiline over time. Bedaquiline effectively inhibits 2D growth in MDA-MB-231 cells, in a time-dependent manner, at a concentration of 10 μM. No effect was observed in MCF10A, which is considered a normal control human mammary epithelial cell line. Unpaired t-test *$p<0.05$, **$p<0.005$. This shows that treatment with Bedaquiline is selective for tumorigenic cells.

Figure 9A:
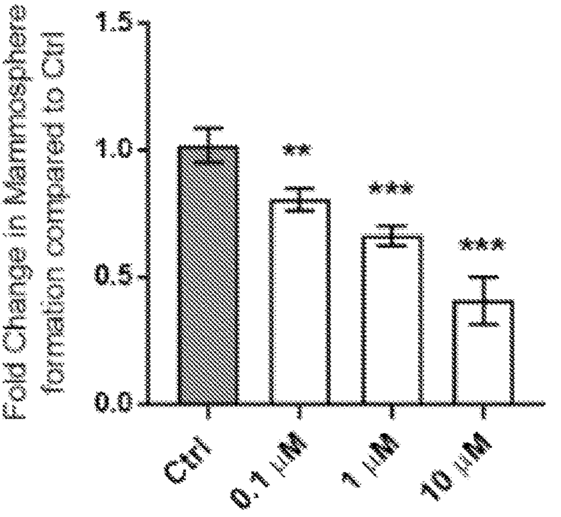
FIG. 9A shows mammosphere formation assay results for different concentrations of Bedaquiline (0.1, 1.0, and 10 μM).

Moreover, ATP-depletion induced by Bedaquiline also inhibited MDA-MB-231 cells from undergoing 3D anchorage-independent growth and cell migration; similarly, Bedaquiline treatment was sufficient to induce cell death, presumably by acting at the level of S-phase, to block cell cycle progression. FIG. 9A shows mammosphere formation assay results for different concentrations of Bedaquiline (0.1, 1.0, and 10 μM). The inhibition of 3D mammosphere formation is concentration-dependent manner, and Bedaquiline effectively blocks 3D mammosphere formation in MDA-MB-231 cells by ~65% at a concentration of 10 μM. One-way ANOVA, Dunnett's multiple comparisons test, $p<0.005$, *$p<0.0005$.

Figure 9B:
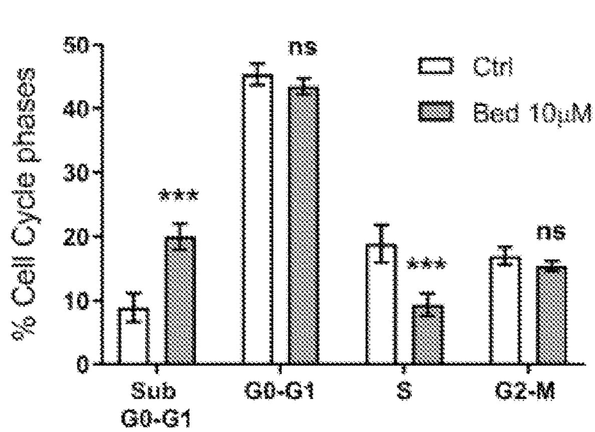
FIG. 9B shows the percentage of cells in each phase of the cell cycle of MDA-MB-231 cells treated with Bedaquiline.
Figures 9C, 9D:
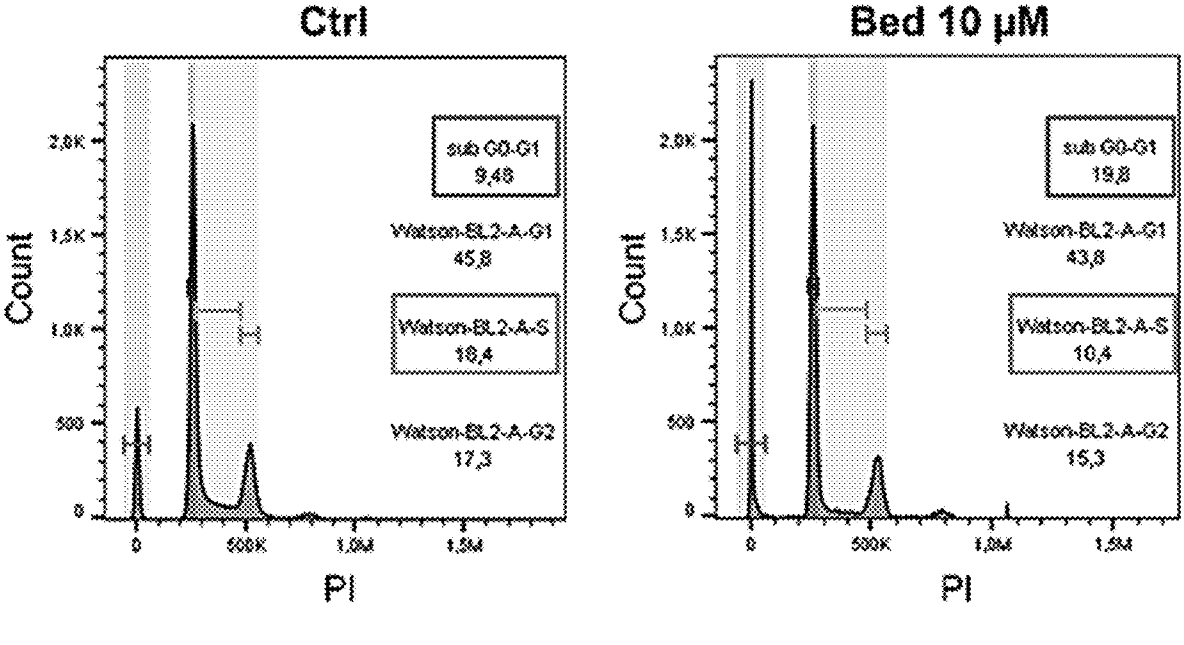
FIGS. 9C and 9D show representative FACS tracings for the control and for cells treated with Bedaquiline, respectively.

ATP-depletion through Bedaquiline also inhibits DNA-synthesis and induces cell death. FIG. 9B shows the percentage of cells in each phase of the cell cycle of MDA-MB-231 cells treated with Bedaquiline. There is a 2-fold reduction of MDA-MB-231 cells in S-phase and a concomitant 2-fold increase in the sub-G0-G1 population, after 120 hours of treatment. Two-way ANOVA, Sidak's multiple comparisons test, ns=not significant, *$p<0.0005$. FIGS. 9C and 9**D show representative FACS tracings for the control and for cells treated with Bedaquiline, respectively.

Figure 9E:
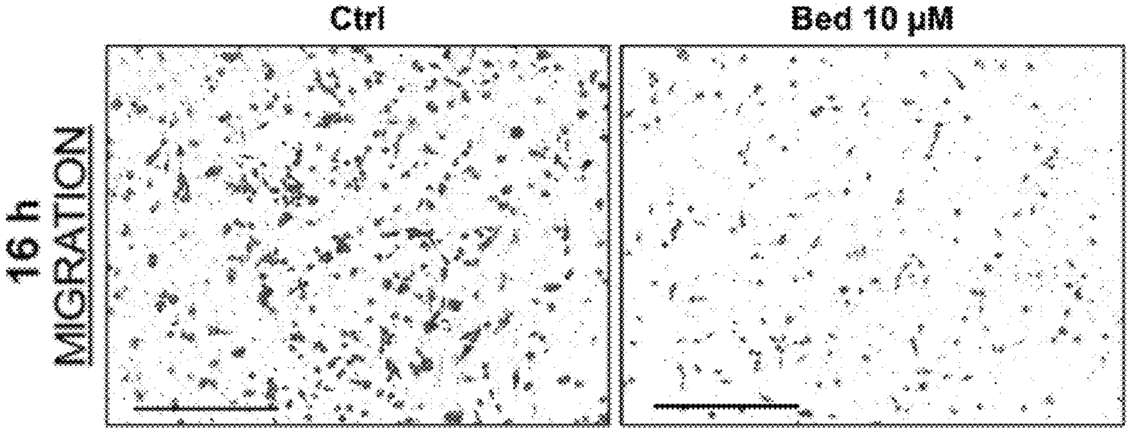
FIG. 9E shows a representative image of migration of MDA-MB-231 cells treated with Bedaquiline, and FIG. 9F expresses the migration relative to the control.

Treatment with Bedaquiline also inhibits cell migration. FIG. 9E shows a representative image of migration of MDA-MB-231 cells treated with Bedaquiline, and FIG. 9F expresses the migration relative to the control. As can be seen, Bedaquiline blocks MDA-MB-231 cell migration by ~50%. MDA-MB-231 cells were cultured in presence of Bedaquiline (10 μM) for 32 hours and moved to the Transwells for 16 hours in presence of Bedaquiline (10 μM). Unpaired t-test, **$p<0.005$.

Figure 10A:
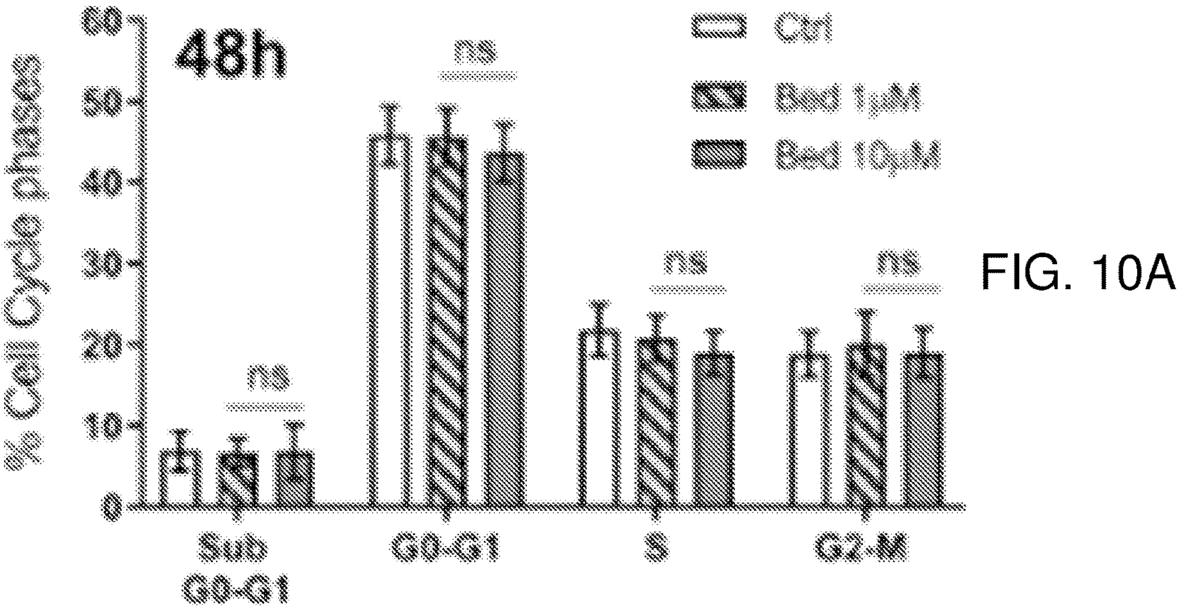
FIGS. 10A-10C show cell cycle populations for MDA-MB-231 cells treated with Bedaquiline (1 and 10 μM) or vehicle alone, after 48, 72 and 120 hours, respectively.
Figure 10B:
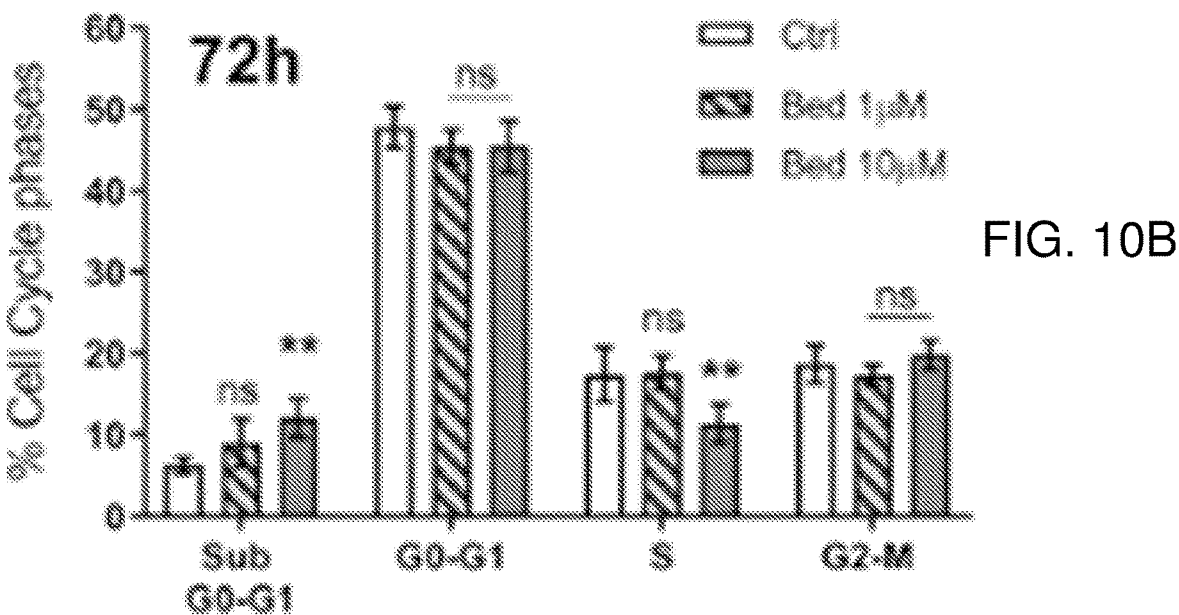
Figure 10C:
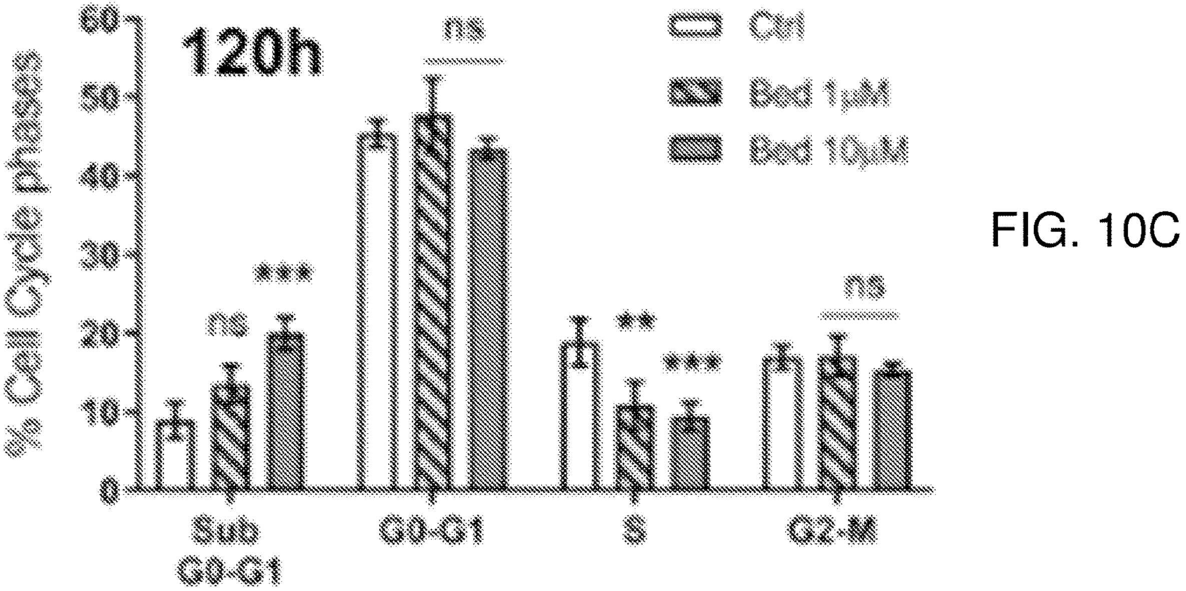

Further cell cycle analysis shows that Bedaquiline treatment of MDA-MB-231 cells specifically reduces the population of S-phase cells and increases cell death, in a dose- and time-dependent manner. FIGS. 10A-10C show cell cycle populations for MDA-MB-231 cells treated with Bedaquiline (1 and 10 μM) or vehicle alone, after 48, 72 and 120 hours, respectively. Cell cycle analysis was performed using FACS. No effects were detectable at 48 hours. However, at 72 and 120 hours, a decrease in the S-phase population and a concomitant increase in the sub-G0-G1 population can be seen in FIGS. 10B and 10C. Two-way ANOVA, Sidak's multiple comparisons test, ns=not significant, *$p<0.01$, $p<0.001$, *$p<0.0005$.

Figure 10D:
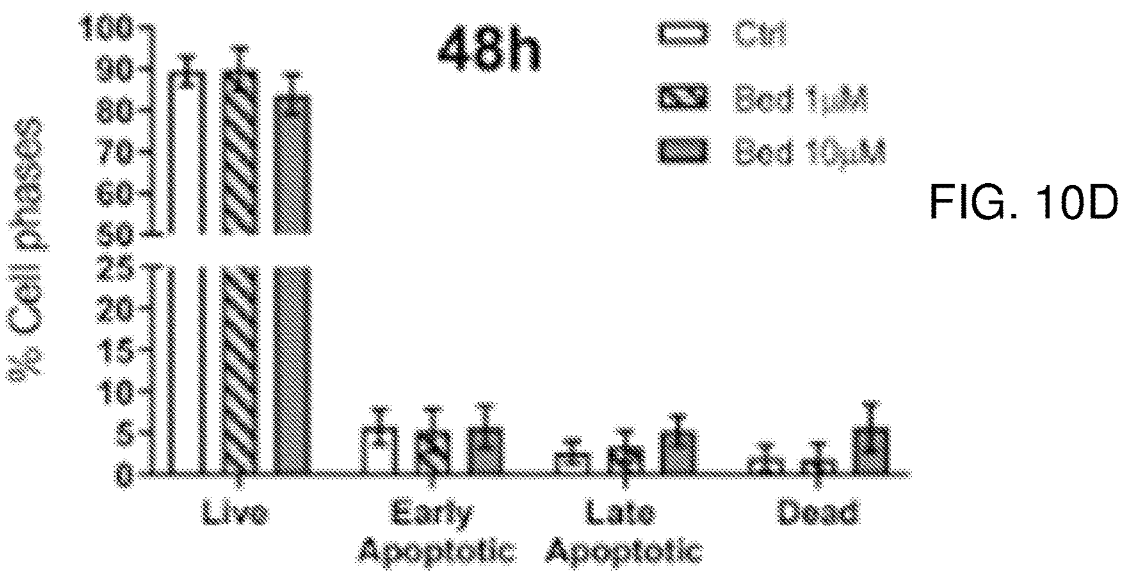
FIGS. 10D-10F show the results of live cell/dead cell analysis. MDA-MB-231 cells were treated with Bedaquiline (1 and 10 μM) or vehicle alone, for 48, 72 and 120 hours, and then subjected to live/dead analysis by FACS.
Figure 10E:
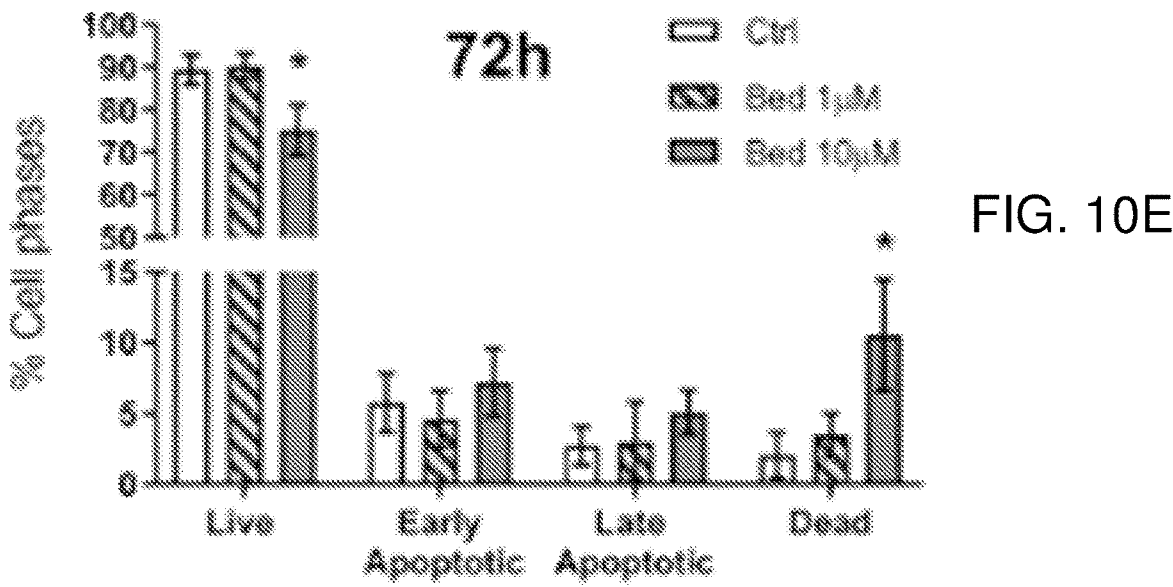
Figure 10F:
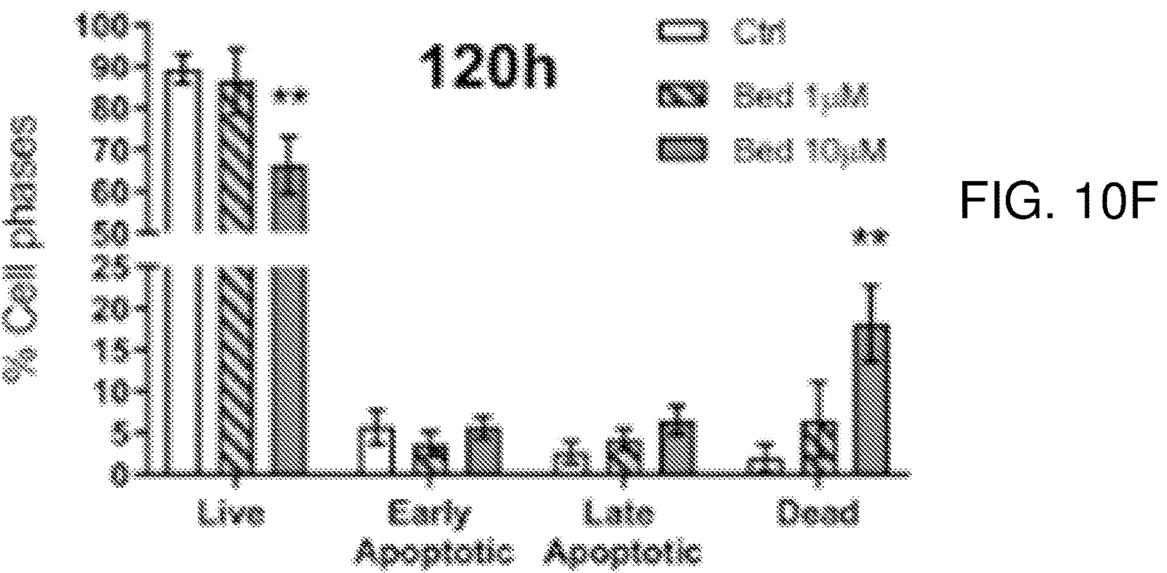

FIGS. 10D-10F show the results of live cell/dead cell analysis. MDA-MB-231 cells were treated with Bedaquiline (1 and 10 μM) or vehicle alone, for 48, 72 and 120 hours, and then subjected to live/dead analysis by FACS. No effects were detectable at 48 hours. However, at 72 and 120 hours (FIGS. 10E and 10F), a decrease in the live cell population and an increase in the dead cell population can be seen. However, no increase in the apoptotic cell population (early or late) was noted, suggesting that cell death was due to necrosis. Two-way ANOVA, Sidak's multiple comparisons test, ns=not significant, *$p<0.01$, $p<0.001$, *$p<0.0005$.

Figure 10G:
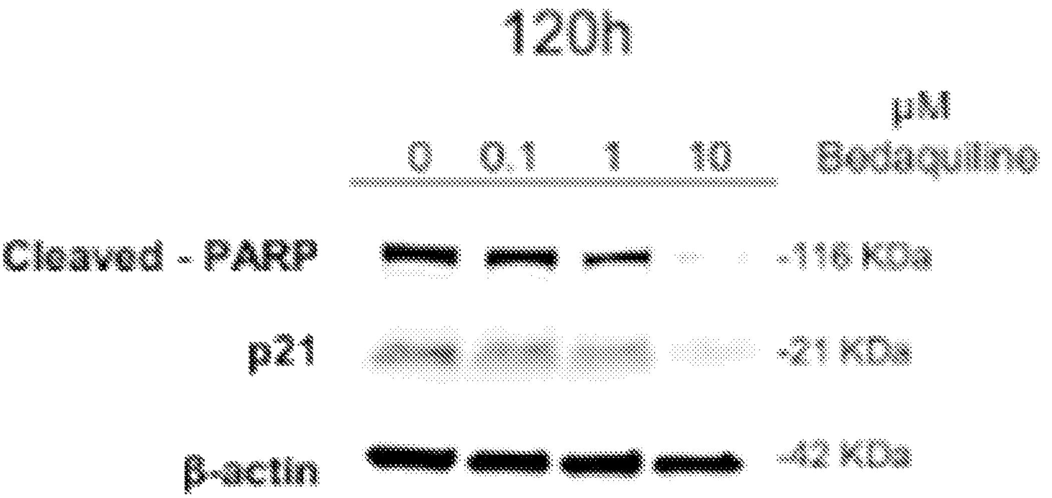
FIG. 10G shows results for a Western blot analysis of the effects of Bedaquiline (0, 0.1, 1 and 10 μM) on PARP and p21 protein expression in MDA-MB, after 120 hours of treatment.

FIG. 10G shows results for a Western blot analysis of the effects of Bedaquiline (0, 0.1, 1 and 10 μM) on PARP and p21 protein expression in MDA-MB, after 120 hours of treatment. Note that PARP and p21 decreased in a concentration-dependent manner. Beta-actin was used as a control for equal loading.

Figures 9F, 11A:
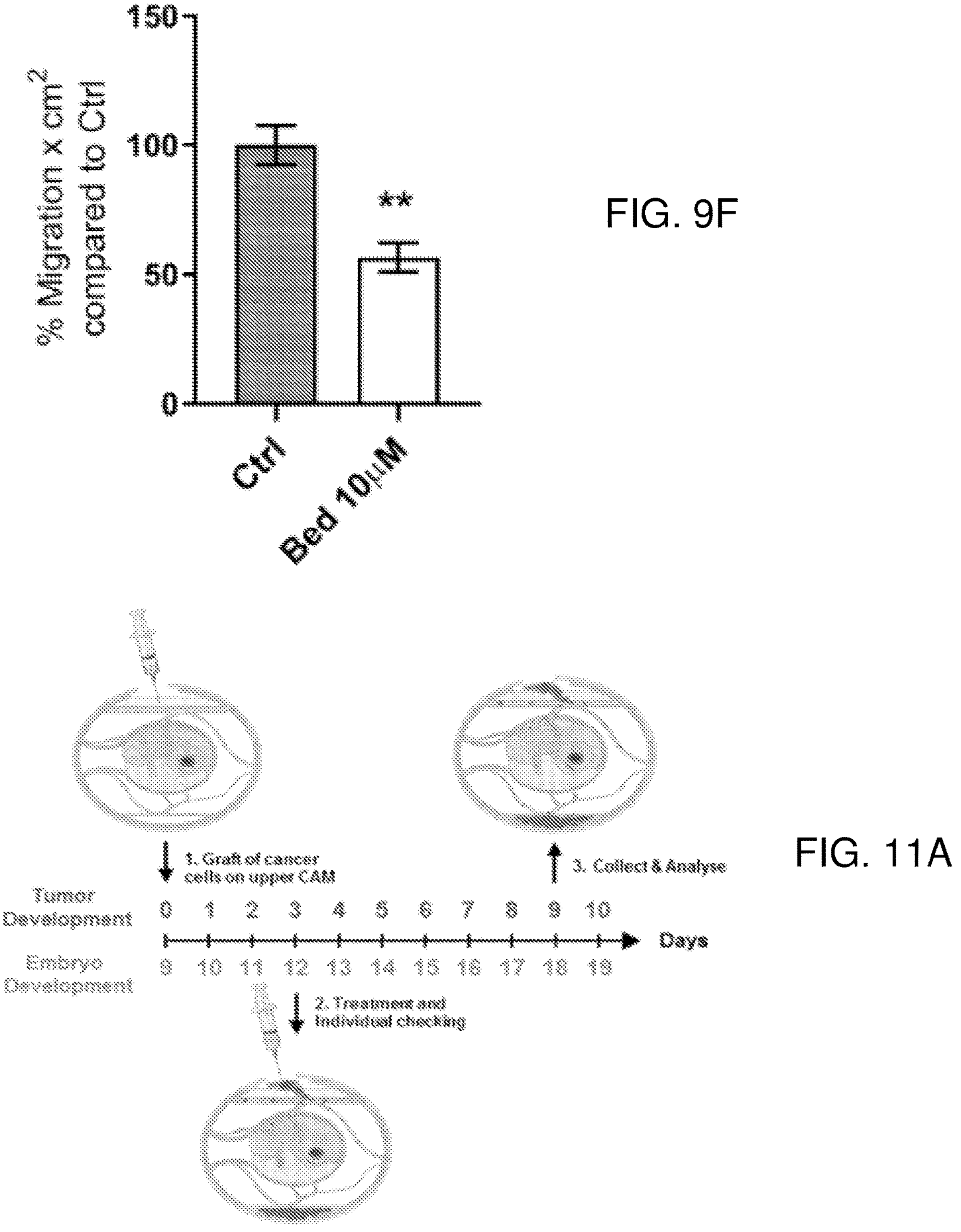
FIG. 11A illustrates the timeline for the CAM assay.

Next, to test in vivo activity, the well-established CAM assay was used with MDA-MB-231 cells, to measure the effect of Bedaquiline effects on tumor growth, spontaneous metastasis and embryo toxicity. FIG. 11A illustrates the timeline for the CAM assay. An inoculum of $1\times10^6$ MDA-MB-231 cells was added onto the CAM of each egg (day E9) and then eggs were randomized into groups. On day E10, tumors were detectable and they were then treated daily for 8 days with vehicle alone (1% DMSO in PBS) or Bedaquiline. After 8 days of drug administration, on day E18, all tumors were weighed, and the lower CAM was collected to evaluate the number of metastatic cells, as analyzed by qPCR with specific primers for Human Alu sequences. Before each drug administration, treatment tolerability was evaluated by scoring the number of live and dead chicken embryos.

Figure 11B:
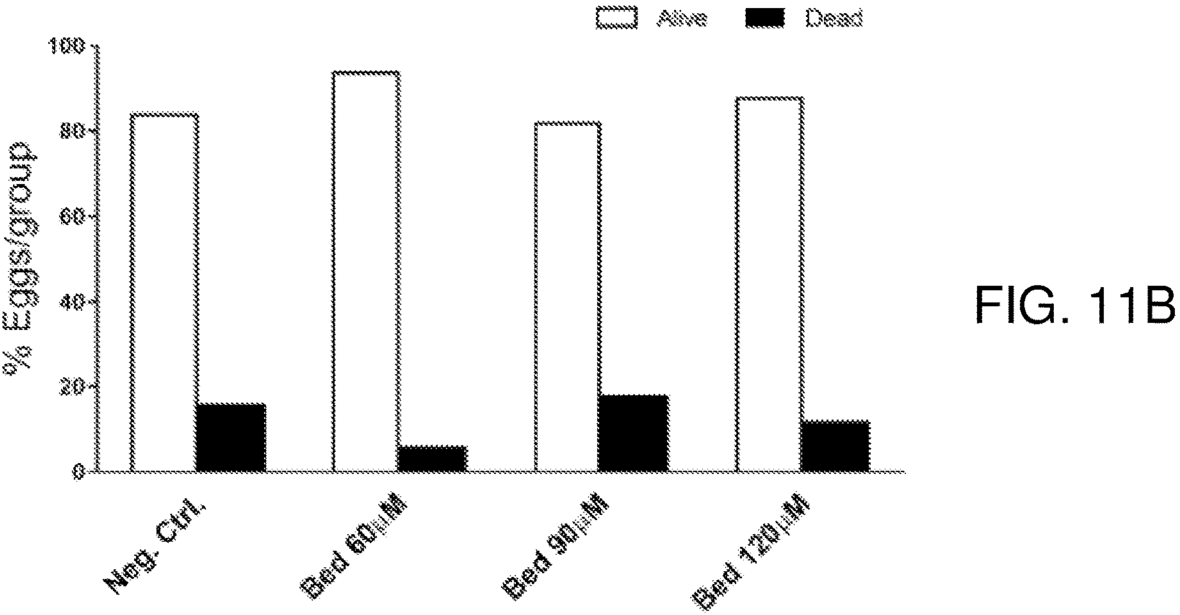
FIG. 11B shows the number of eggs surviving for each treatment in the CAM assay.
Figure 11C:
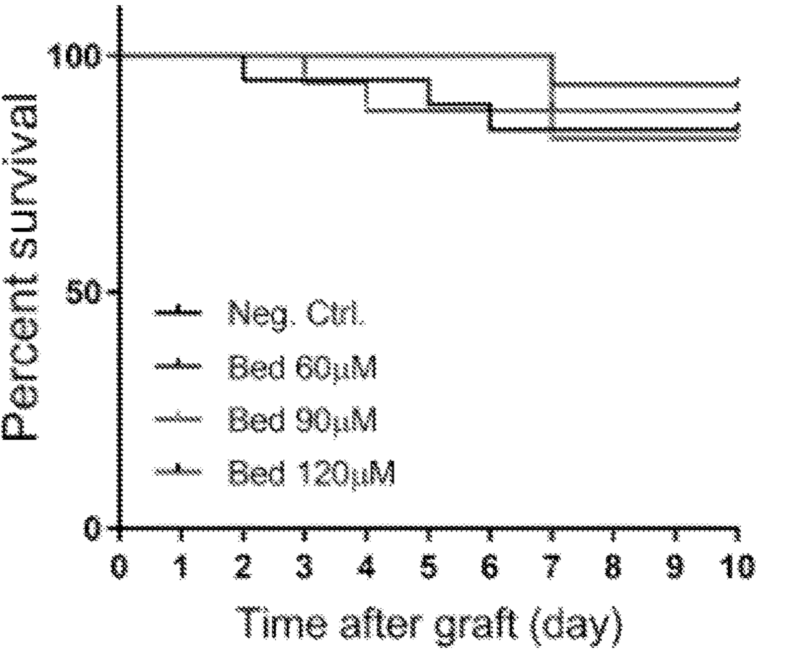
FIG. 11C shows the same data as a percentage survival.
Figure 11D:
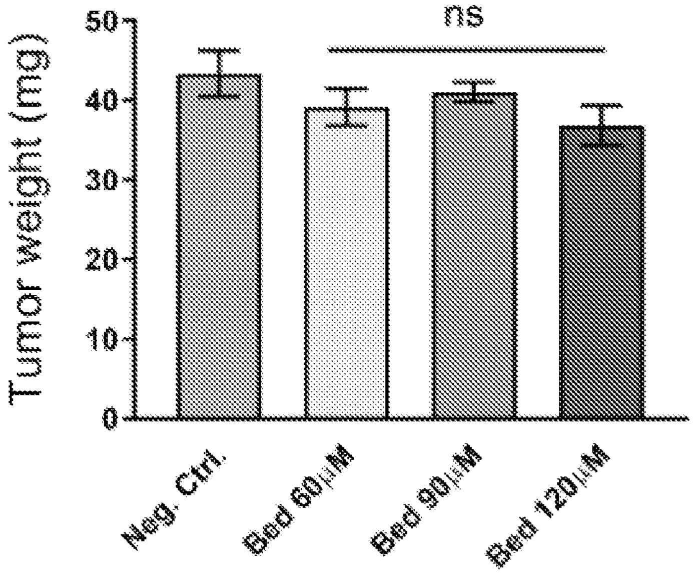
FIG. 11D shows the average tumor weight following each treatment.
Figure 11E:
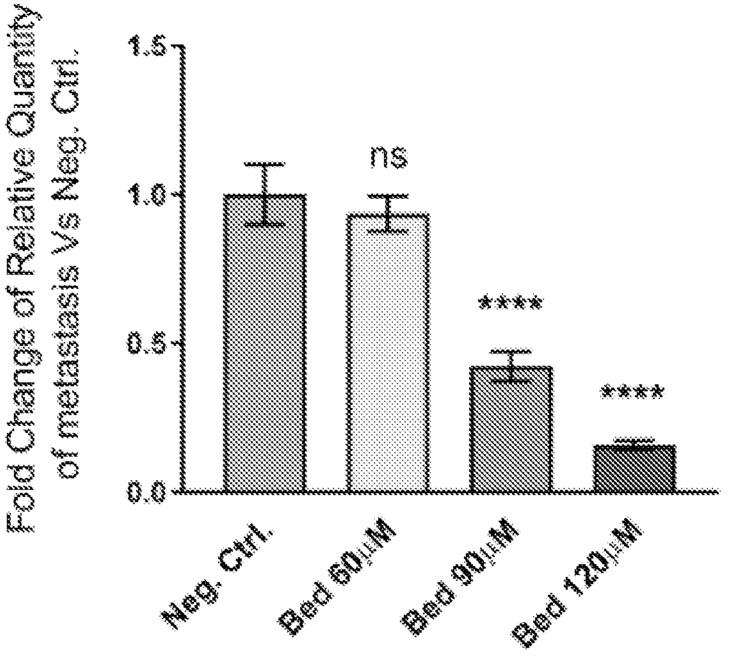
FIG. 11E shows the relative quantity of metastasis for each treatment, as compared to the control.

FIG. 11B shows the number of eggs surviving for each treatment, and FIG. 11C shows the same data as a percentage survival. The data shows that Bedaquiline treatment was not toxic for the chick embryos, at all of the concentrations tested in vivo. FIG. 11D shows the average tumor weight following each treatment. Bedaquiline had no statistically significant effect on tumor growth. In striking contrast, however, Bedaquiline dose-dependently inhibited spontaneous metastasis, by up to 84% at the 120 μM treatment. FIG. 11E shows the relative quantity of metastasis for each treatment, as compared to the control. The results show that pharmacological targeting of the mitochondrial ATP-synthase with Bedaquiline can selectively prevent tumor cell metastasis, without driving toxicity, by inducing ATP-depletion.

It should be appreciated that Bedaquiline is available in a salt form (e.g., Bedaquiline fumarate) and a free-base form. The latter may be more effective than the former, with respect to inducing mitochondrial ATP-depletion in CSCs. Further evaluation of the relative effectiveness and minimum inhibitory concentration are underway.

The data discussed above relate to the unconjugated Bedaquiline compound. It should be appreciated that Bedaquiline can be conjugated with a fatty acid to increase mitochondrial uptake and, as a consequence, the inhibitory strength of the compound. The fatty acid moiety allows the therapeutic agent to more effectively penetrate the mitochondrial membrane and accumulate in cellular mitochondria. Additionally, the increased metabolism of CSCs causes the Bedaquiline-fatty acid conjugates to show a preference for CSCs over normal, healthy cells. Initial evaluation indicates that effectiveness of the Bedaquiline derivatives described herein are from 10% to an order of magnitude or more, improved, when compared to the unconjugated Bedaquiline compound. For example, initial assessments of Bedaquiline derivatives having structures [3B], [4B], and [5]; described below, indicate that these Bedaquiline derivatives are at least 2- to 5-fold more potent than unconjugated Bedaquiline, with respect to inducing ATP-depletion, inhibiting mammosphere formation, and inhibiting spontaneous metastasis.

In some embodiments, the fatty acid moiety may be conjugated via amide bond at the dimethyl amino group. The generic structure [2A], below, illustrates Bedaquiline with a fatty acid moiety at this location, where n is an integer from 1 to 18.

[2A]

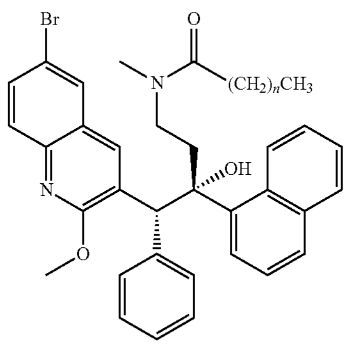

In preferred embodiments, n may be from 3 to 16, and more preferably from 5 to 14, and more preferably 12 to 14. The structure [2B], shown below, illustrates a preferred embodiment, in which n is 12, resulting in a myristic acid moiety conjugated with Bedaquiline.

[2B]

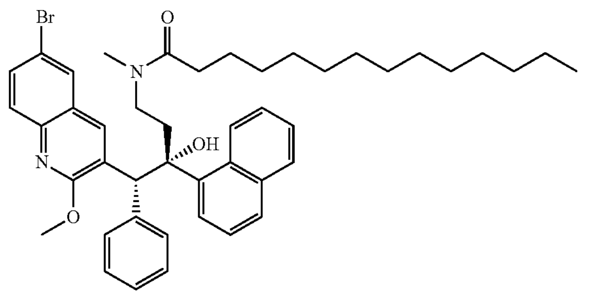

In some embodiments, the fatty acid moiety may be conjugated via carboxyl bond through removal of the halogen. The generic structure [3A], shown below, illustrates Bedaquiline with a fatty acid moiety at this location, where:

R may be H, substituted or unsubstituted C1-C6 straight alkyl, substituted or unsubstituted C1-C6 branched alkyl, substituted or unsubstituted aryl, substituted or unsubstituted heteroaryl, substituted or unsubstituted cycloalkyl, substituted or unsubstituted heterocycle;

n is an integer from 1 to 18, and preferably 5 to 16, and more preferably 12 to 14;

m is an integer from 1 to 12, and preferably 1 to 4; and

A may be absent or may be C, O, N, or S, protonated as necessary to satisfy valence.

[3A]

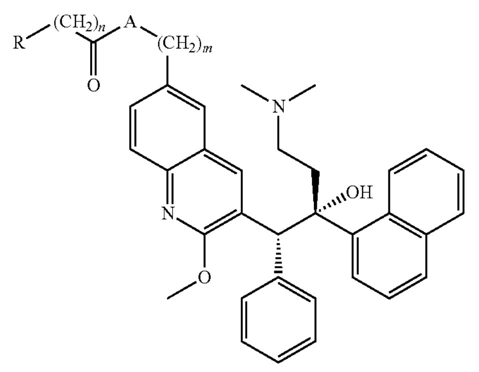

The structure [3B], shown below, illustrates a preferred embodiment, in which R is methyl, n is 12, m is 4, and A is O, resulting in a myristic acid moiety conjugated with Bedaquiline, also referred to herein as a Bedaquiline derivative with a fatty acid moiety.

[3B]

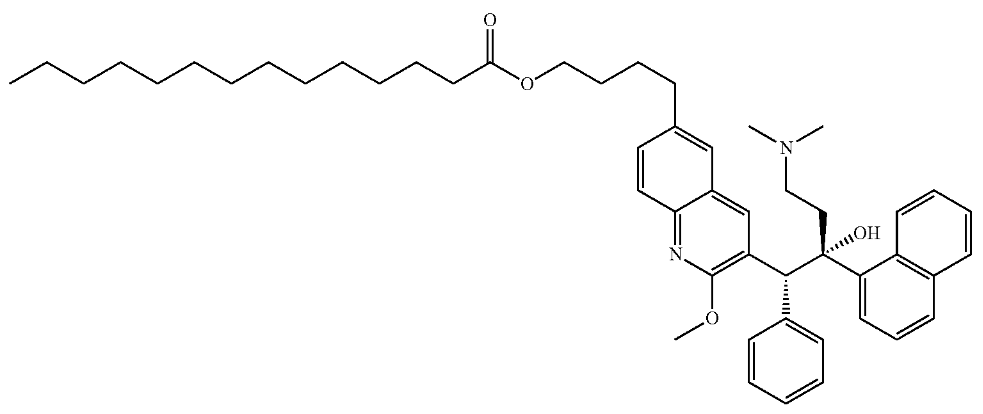

In some embodiments, the fatty acid moiety may be conjugated via carboxyl bond through removal of the halogen, and include an additional B species before the aliphatic tail. The generic structure [4A], shown below, illustrates Bedaquiline derivatives with a fatty acid moiety at this location and having an additional species B in the aliphatic tail. In structure [4A], R may be H, substituted or unsubstituted C1-C6 straight alkyl, substituted or unsubstituted C3-C6 branched alkyl, substituted or unsubstituted aryl, substituted or unsubstituted heteroaryl, substituted or unsubstituted cycloalkyl, substituted or unsubstituted heterocycle;

n is an integer from 1 to 18, and preferably 5 to 16, and more preferably 12 to 14;

m is an integer from 1 to 12, and preferably 1 to 4;

A may be absent or may be C, O, N, or S, protonated as necessary to satisfy valence; and B may be absent or may be C, O, N, or S, protonated as necessary to satisfy valence.

[4A]

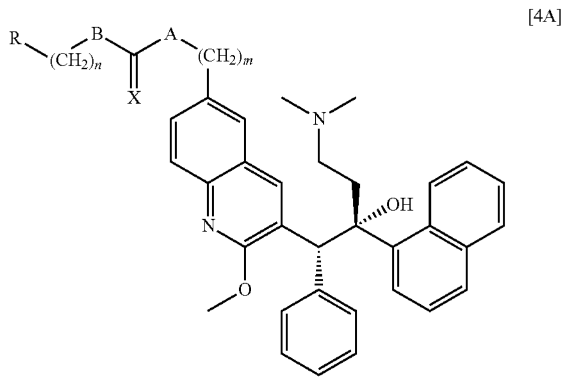

Structure [4B], shown below, illustrates another preferred embodiment of a Bedaquiline derivative with a fatty acid moiety. In this embodiment, R is methyl, n is 12, b is 4, A is O, and B is absent, resulting in a myristic acid moiety conjugated with Bedaquiline. Structure [4B] exhibits significant improvements of at least 2-5 fold, compared to unconjugated Bedaquiline, in properties such as ATP inhibition, 3D mammosphere formation inhibition, and reduction in relative quantity of metastasis (i.e., through the CAM assay).

It should be appreciated that the conjugated compounds described herein may be synthesized from Bedaquiline using common synthesis techniques known in the art. A demonstrative synthesis scheme is set forth below, beginning with Bedaquiline.

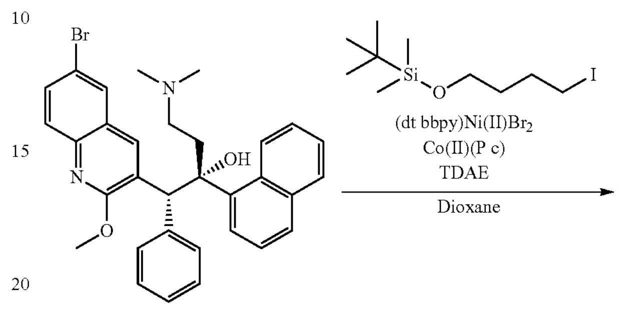

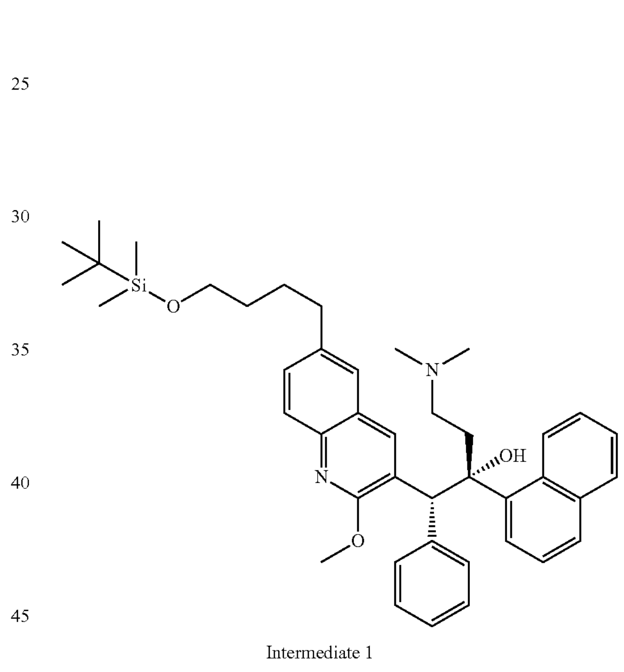

Intermediate 1

[4B]

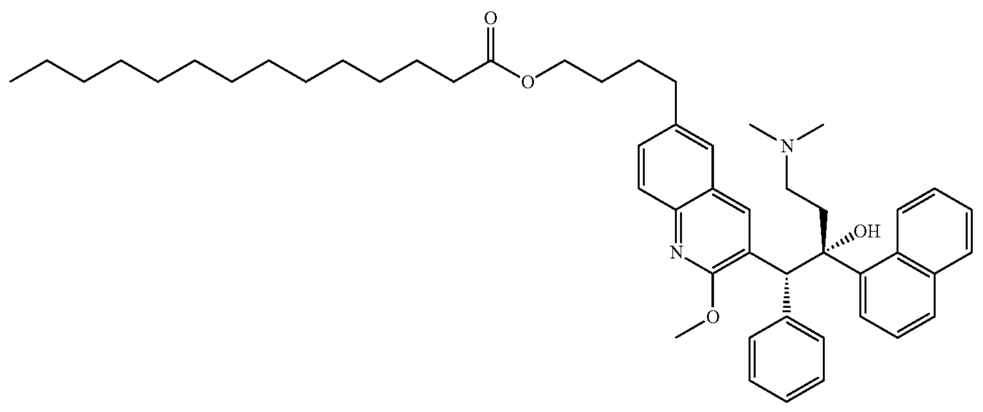

-continued

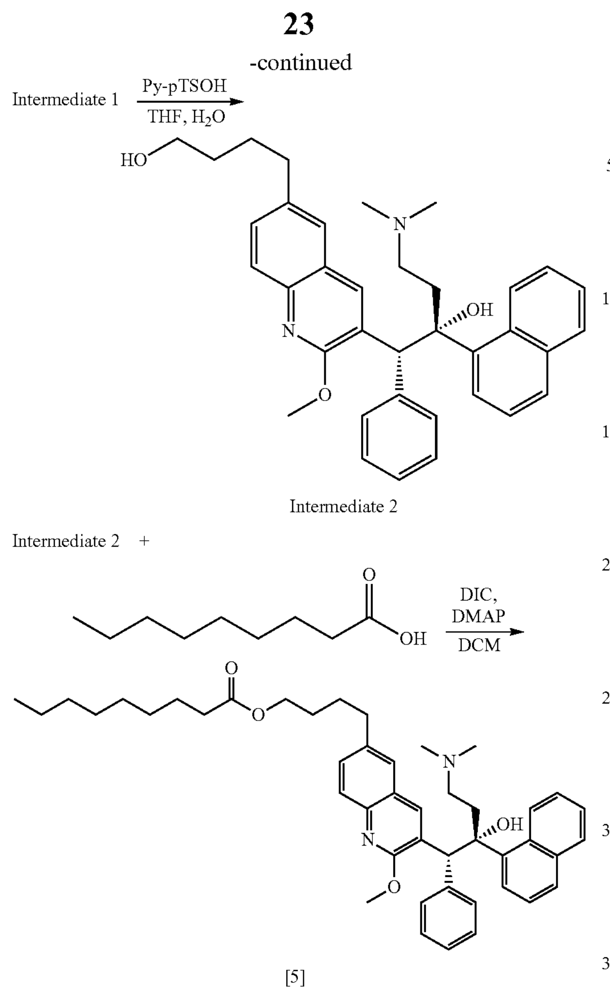

Intermediate 2

Intermediate 2 +

[5]

The example synthesis scheme above results in structure [5], in which R is methyl, B is absent, n is 7, and m is 4. Early assessment of compound of structure [5] indicates that this Bedaquiline derivative is at least 5-fold more potent than unconjugated Bedaquiline, at ATP-depletion, inhibiting mammosphere formation, and inhibiting spontaneous metastasis. It should be appreciated that the fatty acid moiety in the final reaction determines the alkyl chain length in the resulting Bedaquiline derivative. Other ATP-synthase inhibitors that may be used in this approach include Resveratrol, Trans-Resveratrol, Quercetin, Piceatannol, Bz 423 (also known as 7-Chloro-1,3-dihydro-5-(4-hydroxyphenyl)-1-methyl-3-(2-naphthalenylmethyl)-2H-1,4-benzodiazepin-2-one), and Gboxin (an oxidative phosphorylation inhibitor, also known as 2-ethyl-1-methyl-3-[2-[[(1R,2S,5R)-5-methyl-2-(1-methylethyl)cyclohexyl]oxy]-2-oxoethyl]-1H-benzimidazolium).

Although the data disclosed herein is predominantly based on breast cancer cell lines, the compounds of the present approach have efficacy for other types of cancer. In prior work, the inventors demonstrated that mitochondrial biogenesis inhibitors successfully inhibited tumor-sphere formation in a wide-variety of cell lines from several tumor types. Table 12, below, lists cancer cell lines that have been shown to be susceptible to mitochondrial biogenesis inhibitors. This illustrates that a wide variety of cancer types are highly dependent upon ATP for growth, including tumor recurrence and metastasis. Inhibiting ATP production in CSCs in these cancer types would therefore be expected to inhibit mammosphere formation and, consequently, prevent and/or reduce the likelihood of tumor recurrence and/or metastasis. Thus, given these results, the present approach is effective for numerous cancer types.

TABLE 12

Inhibiting mitochondrial biogenesis is effective against a variety of cancer types.

| Cancer Type | Cell Line(s) |
|---|---|
| Breast (ER+) | MCF7 |
| | T47D |
| Breast (ER−) | MDA-MB-231 |
| DCIS | MCF10.DCIS.com ("pre-malignant") |
| Ovarian | SKOV3 |
| | Tov21G |
| | ES2 |
| Prostate | PC3 |
| Pancreatic | MIA PaCa2 |
| Lung | A549 |
| Melanoma | A375 |
| Glioblastoma | U-87 MG |

The following paragraphs describe the materials and assays used to generate the data described herein. It should be appreciated that the person having an ordinary level of skill in the art may perform the same assays as described herein, and/or may utilize other assays generally known in the art to assess the physical, chemical, and pharmaceutical properties of a compound as described herein.

Bioinformatic Analysis: Unbiased label-free proteomics, comparing 2D-monolayers and 3D-mammospheres, was carried out using MCF7 and T47D breast cancer cell lines. It should be appreciated that other cell lines may be used without departing from the present approach. Informatics analysis was performed using a variety of publicly available of GEO DataSets (GSE36953; GSE2034; GSE59000; GSE55470), archived in the NCBI database, and related to 3D growth, metastasis and circulating tumor cells (CTCs). Gene expression profiling data was extracted from these GEO DataSets. HeatMaps were generated with QIAGEN OmicSoft Suite Software. Volcano plots were produced by examining the annotations present in OncoLand Metastatic Cancer (QIAGEN OmicSoft Suite). In addition, functional "core analyses" were performed using Ingenuity Pathway Analysis Software (IPA; QIAGEN), on annotated genes. Gene co-expression profiles were extracted from The Metastatic Breast Cancer Project Provisional (2020), using cBioPortal (https://www.cbioportal.org/); mRNA expression profiling (RNA Seq V2 RSEM) was carried via RNA-sequencing of metastatic breast cancer samples from 146 patients.

Kaplan-Meier (K-M) analysis were performed on ATP5F1C. An open-access online survival analysis tool was used to interrogate publicly-available microarray data from up to 3,951 breast cancer patients. For this purpose, data from ER(+) patients were analyzed. Biased array data were excluded from the analysis. This allowed the identification of ATP5F1C (also known as ATP5C1), as a significant prognostic marker. Hazard-ratios were calculated at the best auto-selected cut-off, and p-values were calculated using the Log-rank test and plotted in R. K-M curves were generated online using the K-M-plotter (as high-resolution TIFF files), using univariate analysis: https://kmplot.com/analysis/index.php?p=service&cancer=breast. This approach allowed for directly performing in silico validation of ATP5F1C as a marker of tumor recurrence (RFS, relapse-free survival) and distant metastasis (DMFS, distant metastasis-free survival). The latest 2020 version of the database was utilized for all these analyses.

Reagents and Model Cell Lines: It should be apparent that other cell lines may be used without departing from the present approach. BioTracker ATP-Red 1 (#SCT045) was obtained commercially from Merck-Millipore, Inc. The triple-negative human breast cancer cell line, MDA-MB-231, was obtained from the American Type Culture Collection (ATCC). MCF10A cells, a non-tumorigenic human breast epithelial cell line, were also obtained from ATCC. MDA-MB-231 cells were cultured in DMEM (High Glucose) supplemented with 10% Fetal Bovine Serum (FBS, Sigma Aldrich), 2 mM Glutamax (Gibco, Life Technologies, Waltham, MA, USA), and 1% penicillin/streptomycin (Gibco, Life Technologies). The MCF10A cell line was maintained in a mammary epithelial cell growth medium (MEGM; Lonza, Basel, Switzerland) supplemented with 0.4% Bovine pituitary extract (BPE), 0.1% insulin, 0.1% hEGF, 0.1% Hydrocortisone, 0.1% GA-1000, and 100 ng/mL of cholera toxin. All cell lines were cultured at 37° C. in 5% $CO_2$ in a humidified atmosphere.

ATP assay using BioTracker ATP-Red 1: Cells were stained with BioTracker ATP-Red 1 after various treatments. After 30 minutes of incubation, the cells were washed twice with DPBS, collected and dissociated into a single-cell suspension with a 40 μm cell strainer. The cells were analyzed using the Attune N×T Flow Cytometer. Means of the signal (at 570 nm) were compared.

3D Anchorage Independent Growth Assay: This assay is also referred to as the mammosphere formation assay. A single-cell suspension was prepared using enzymatic, and manual disaggregation (25-g needle). Then, cells were plated at a density of 500 cells/$cm^2$ in mammosphere medium (DMEM-F12+1X B-27 Plus Supplement+20 ng/ml EGF+Pen/Strep) under non-adherent conditions, in culture dishes pre-coated with (2-hydroxyethylmethacrylate) (poly-HEMA, Sigma Aldrich Inc.), called “mammosphere plates.” Cells were grown for 5 days and maintained in a humidified incubator at 37° C. After 5 days of culture, 3D-mammospheres >50 μm were counted using an eye piece (“graticule”), and the percentage of cells plated which formed spheres was calculated and is referred to as percent mammosphere formation, and was normalized to one (1=100% MFE). 3D mammosphere formation efficiency (MFE) was analyzed in both the ATP-low and ATP-high sub-populations of cells. All 3D mammosphere experiments were performed in triplicate, at least 3 times independently.

shRNA Lentiviral transduction: Lentiviral plasmids, packaging cells and reagents were purchased from Genecopoeia. Forty-eight hours after seeding, 293Ta packaging cells were transfected with lentiviral vectors encoding an shRNA clone set of 3 constructs against all 3 variants for human ATP5F1C, in a lentiviral psi-LVRInU6TGP vector, with an inducible U6 promoter, CMV promoter-TetR-SV40 promoter-eGFP-IRES-puromycin. A scrambled control psi-LVRInU6TGP vector (sh-Control) was transfected in parallel. Two days post-transfection, lentivirus-containing culture medium was passed through a 0.45 μm filter and added to the target cells (MDA-MB-231), in the presence of 5 μg/ml Polybrene. Infected cells were selected, with a concentration of 1.5 μg/ml of puromycin.

Western Blotting: Cells were lysed in RIPA buffer (Sigma Aldrich, Inc.) containing one tablet of Complete TM inhibitor mix (Roche Applied Science, Indianapolis) and one tablet of PhosSTOP™ phosphate inhibitors per 10 mL of buffer and loaded onto SDS-polyacrylamide gels. The gels were transferred to 0.2 μm nitrocellulose membranes, using the Trans-Blot Turbo Transfer System (Bio-Rad, Inc.) Membranes were incubated with the respective primary antibodies diluted in Tris-buffered saline, 0.1% Tween 20 (Sigma Aldrich, Inc.) and 5% Bovine Serum Albumin (BSA; Sigma Aldrich Inc.) (TBST), and incubated overnight at 4° C. Then, the blots were washed and incubated with appropriate secondary antibodies and detected using Super Signal West Pico Chemiluminescent Substrate (Thermo Scientific, Inc.), using the G-Box (Syngene, Inc). Antibodies and their dilutions used for Western blot analysis were as follows: mouse anti-ATP5F1C 1:500, mouse anti-β-actin 1:10,000, rabbit anti-PARP 1:1,000, rabbit anti-p21 1:1,000. The resulting immune-blot images were acquired using GeneSys Software (Syngene, Inc.).

Cell Cycle Analysis by FACS: Cell-cycle analysis was performed on the ATP-high and ATP-low cell sub-populations, by FACS analysis using the Attune N×T Flow Cytometer. Briefly, after trypsinization, the re-suspended cells were incubated with propidium iodide, as per the manufacturer's recommendations (Merck Millipore, Inc.). At least 25,000 events were analyzed per condition. Gated cells were categorized into cell-cycle stages.

Cell Migration Assays: Briefly, $3.5\times10^4$ cells in 0.5 ml of serum-free DMEM with 0.1% BSA were added to the wells of 8-μm pore, non-coated membrane modified Boyden chambers (Transwells). The lower chambers contained 10% fetal bovine serum in DMEM to serve as a chemo-attractant. Cells were incubated at 37° C. and allowed to migrate throughout the course of 16 hours. Noninvasive cells were removed from the upper surface of the membrane by scrubbing with cotton swabs. Chambers were stained in 0.5% crystal violet diluted in 100% methanol for 30-60 min, rinsed in water and examined under a bright-field microscope. Values for invasion and migration were obtained by counting five fields per membrane (20× objective) and represent the average of three independent experiments.

Tumor Growth, Metastasis and Embryo Toxicity Assays: Xenograft assays were carried out by INOVOTION (Société: 811310127), La Tronche-France. Fertilized White Leghorn eggs were incubated at 37.5° C. with 50% relative humidity for 9 days. At that moment (E9), the chorioallantoic membrane (CAM) was dropped down by drilling a small hole through the eggshell into the air sac, and a 1 $cm^2$ window was cut in the eggshell above the CAM. The MDA-MB-231 tumor cell line was cultivated in DMEM medium supplemented with 10% FBS and 1% penicillin/streptomycin. On day E9, cells were detached with trypsin, washed with complete medium and suspended in graft medium. An inoculum of $1\times10^6$ MDA-MB-231 cells was added onto the CAM of each egg (E9) and then eggs were randomized into groups. On day E10, tumors were detectable, and they were then treated daily for 8 days with vehicle alone (1% DMSO in PBS) or with three different dosages of Bedaquiline or a Bedaquiline conjugate as described herein. At day 18 (E18), the upper portion of the CAM was removed from each egg, washed in PBS and then directly transferred to paraformaldehyde (fixation for 48 h) and weighed. For tumor growth assays, at least 14 tumor samples were collected and analysed per group (N≥14). On day E18, a 1 $cm^2$ portion of the lower CAM was collected to evaluate the number of metastatic cells in at least 7 samples per group (N≥7). Genomic DNA was extracted from the CAM (commercial kit) and analyzed by qPCR with specific primers for Human Alu sequences. Calculation of Cq for each sample, mean Cq and relative amounts of metastases for each group are directly managed by the Bio-Rad® CFX Maestro software. A one-way ANOVA analysis with post-tests was performed on all the data. Before each administration, the treatment tolerability was evaluated by scoring the number of live and dead embryos.

Statistical Analysis: All analyses were performed with GraphPad Prism 6. Data were represented as mean±SD (or ±SEM where indicated). All experiments were conducted at least 3 times independently, with >3 technical replicates for each experimental condition tested (unless stated otherwise, e.g., when representative data is shown). Statistically significant differences were determined using the Student's t-test or the analysis of variance (ANOVA) test. For the comparison among multiple groups, one-way ANOVA was used to determine statistical significance. $p<0.05$ was considered significant.

It should be appreciated that some embodiments of the present approach may take the form of a pharmaceutical composition, such as a composition for preventing and/or reducing the likelihood of metastasis. Pharmaceutical compositions of the present approach may include Bedaquiline or a Bedaquiline derivative with a fatty acid (including salts thereof) as an active compound, in any pharmaceutically acceptable carrier. If a solution is desired, water may be the carrier of choice for water-soluble compounds or salts. With respect to water solubility, organic vehicles, such as glycerol, propylene glycol, polyethylene glycol, or mixtures thereof, can be suitable. Additionally, methods of increasing water solubility may be used without departing from the present approach. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized. The present approach is not intended to be limited to a particular form of administration, unless otherwise stated.

In addition to the active compound, pharmaceutical formulations of the present approach can contain other additives known in the art. For example, some embodiments may include pH-adjusting agents, such as acids (e.g., hydrochloric acid), and bases or buffers (e.g., sodium acetate, sodium borate, sodium citrate, sodium gluconate, sodium lactate, and sodium phosphate). Some embodiments may include antimicrobial preservatives, such as methylparaben, propylparaben, and benzyl alcohol. An antimicrobial preservative is often included when the formulation is placed in a vial designed for multi-dose use. The pharmaceutical formulations described herein can be lyophilized using techniques well known in the art.

In embodiments involving oral administration of an active compound, the pharmaceutical composition can take the form of capsules, tablets, pills, powders, solutions, suspensions, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc may be included for tableting purposes. Solid compositions of a similar type may be employed as fillers in soft and hard-filled gelatin capsules. Materials in this connection also include lactose or milk sugar, as well as high molecular weight polyethylene glycols. When aqueous suspensions and/or elixirs are desired for oral administration, the compounds of the presently disclosed subject matter can be combined with various sweetening agents, flavoring agents, coloring agents, emulsifying agents and/or suspending agents, as well as such diluents as water, ethanol, propylene glycol, glycerin and various like combinations thereof.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

With respect to pharmaceutical compositions, the pharmaceutically effective amount of the active compound described herein (e.g., Bedaquiline or a Bedaquiline derivative with a fatty acid moiety) will be determined by the health care practitioner, and will depend on the condition, size and age of the patient, as well as the route of delivery. In one non-limiting embodiment, a dosage from about 0.1 to about 200 mg/kg has therapeutic efficacy, wherein the weight ratio is the weight of the active compound, including the cases where a salt is employed, to the weight of the subject. In some embodiments, the dosage can be the amount of active compound needed to provide a serum concentration of the active compound of up to between about 1 and 5, 10, 20, 30, or 40 μM. In some embodiments, a dosage from about 1 mg/kg to about 10, and in some embodiments about 10 mg/kg to about 50 mg/kg, can be employed for oral administration. Typically, a dosage from about 0.5 mg/kg to 5 mg/kg can be employed for intramuscular injection. In some embodiments, dosages can be from about 1 μmol/kg to about 50 μmol/kg, or, optionally, between about 22 μmol/kg and about 33 μmol/kg of the compound for intravenous or oral administration. An oral dosage form can include any appropriate amount of active compound, including for example from 5 mg to, 50, 100, 200, or 500 mg per tablet or other solid dosage form.

Pharmaceutical compositions may employ an active compound as a free base or as a salt. Common salts include monohydrate and hyclate, the latter of which may be useful for improving solubility. Demonstrative pharmaceutical compositions are provided, which are meant to be non-limiting examples only. In capsule form, the composition may include 50 mg or 100 mg of the active compound as a base. The other ingredients may include gelatin, magnesium stearate, shellac glaze, sodium lauryl sulfate, starch, quinoline yellow (E104), erythrosine (E127), patent blue V (E131), titanium dioxide (E171), iron oxide black (E172), and propylene glycol. A delayed-release tablet form may include 60 mg or 120 mg of the active compound, and 3.6 mg or 7.2 mg, respectively, of sodium, and inactive ingredients including lactose monohydrate; microcrystalline cellulose; sodium lauryl sulfate; sodium chloride; talc; anhydrous lactose; corn starch; crospovidone; magnesium stearate; and a cellulosic polymer coating. It should be appreciated that other pharmaceutical compositions may be used without departing from the present approach, which is not intended to be limited to any specific formulation.

In some embodiments, the active compound may be present as a salt, such as a fumarate salt. Fumarate salts of the active compound are insoluble in water. In some embodiments, the pharmaceutical composition may be in the form of a tablet, and the active compound may be present with inactive ingredients such as colloidal silicon dioxide, crospovidone, hypromellose 2910, polysorbate 20, silicified microcrystalline cellulose, and sodium stearyl fumarate. In some embodiments, the pharmaceutical composition may be in the form of a tablet, and the active compound may be present with inactive ingredients such as colloidal silicon dioxide, corn starch, croscarmellose sodium, hypromellose 219, lactose monohydrate, magnesium stearate, microcrystalline cellulose, and polysorbate 20. The precise formulations depend on the particular embodiment, and the person having an ordinary level of skill can use formulation methods known and available in the art.

In some embodiments, the present approach may take the form of treatment methods comprising administering to a patient in need thereof of a pharmaceutically effective amount of a one or more pharmaceutical compositions and a pharmaceutically acceptable carrier. For example, the present approach may be used to eradicate a population of CSCs likely to cause metastasis, thereby preventing or reducing the likelihood of metastasis and recurrence from the original CSC population.

The present approach may be used to prevent and/or reduce the likelihood of tumor recurrence, metastasis. Anti-cancer treatments often fail because the tumor recurs or metastasizes, particularly after surgery. CSC mitochondrial activity is, at least in part, responsible for these causes of treatment failure. Embodiments of the present approach may be used in situations where conventional cancer therapies fail, and/or in conjunction with anti-cancer treatments to prevent or reduce the likelihood of failure due to tumor recurrence and/or metastasis. A pharmaceutically effective amount of a pharmaceutical composition containing, as the active compound, Bedaquiline or a Bedaquiline derivative with a fatty acid moiety as described herein, may be administered to a patient. The patient have cancer, or may be at risk of having cancer, or may be at risk of tumor recurrence and/or metastasis.

As described in Applicant's co-pending U.S. Provisional Patent Application Nos. 62/686,881, filed Jun. 19, 2018, and 62/731,561, filed Sep. 14, 2018, and incorporated by reference in their entirety, e-CSCs represent a CSC phenotype associated with proliferation. In addition to bulk cancer cells and CSCs, it should be appreciated that the present approach may be used to target a hyper-proliferative cell sub-population that the inventors refer to as e-CSCs, which show progressive increases in stemness markers (ALDH activity and mammosphere-forming activity), highly elevated mitochondrial mass, and increased glycolytic and mitochondrial activity.

In view of the foregoing, it should be appreciated that the present approach may take a wide variety of forms, depending on the embodiment. For example, embodiments of the present approach may take the form of a composition, and in particular a pharmaceutical composition. The therapeutic compound may be the active ingredient, and may be present in a pharmaceutically-effective amount.

Embodiments of the present approach may also take the form of methods for preventing or reducing the likelihood of at least one of tumor recurrence and metastasis. In some embodiments, an effective amount of a composition having, as its active compound, Bedaquiline may be administered. In some embodiments, an effective amount of a composition having, as its active compound, a Bedaquiline derivative with a fatty acid moiety as described herein, may be administered.

Some embodiments of the present approach may take the form of companion diagnostics, using the ATP-related gene signature described herein. The gene signature may be used as companion diagnostics to identify cancer patients that may benefit from ATP inhibition therapy with Bedaquiline or a Bedaquiline derivative with a fatty acid moiety, as described above. Once identified, candidates may receive a pharmaceutically effective amount of a composition comprising, as an active compound, Bedaquiline or a Bedaquiline derivative with a fatty acid moiety.

A biological epithelial sample of the cancer may be obtained, and the level of each biomarker in the selected gene signature of the biological sample may be determined, using methods for measuring biomarker expression known and available in the art. The determined level is compared to a threshold level for each biomarker in the signature, and a pharmaceutically effective amount of the ATP inhibitor is administered if the determined levels of the biomarkers in the gene signature exceed the threshold level. Preferably, the ATP inhibitor is administered if the determined level for all biomarkers in the gene signature exceeds the threshold level for the biomarker. The threshold level for each biomarker may be determined using a non-cancerous epithelial sample from the same subject.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention, and the claims should not be limited by these terms. These terms are only used to distinguish one element of the invention from another. Thus, a first element discussed below could be termed an element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

The phrase "treatment cycle" refers to a course of treatment, such as a dosing schedule that is repeated on a regular or pre-defined basis. A treatment cycle can comprise several days of treatment followed by several days of rest. For example only, an agent may be administered daily for two weeks, followed by two weeks of no treatment, over a 4-week treatment cycle. It should be appreciated that a treatment cycle may depend on a number of factors, such as the disease state, age, sex, and weight of the individual, as well as the particular agent(s) and/or methodologies, to elicit a desired response in the individual.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method for treating at least one of tumor recurrence and metastasis in a subject, the method comprising:

administering to the subject a pharmaceutically effective amount an active compound having the structure:

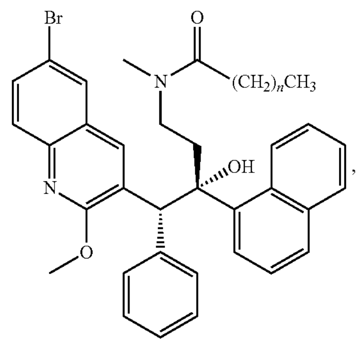

wherein n is an integer from 3 to 18.

2. The method of claim 1, wherein n is an integer from 5 to 14.

3. The method of claim 2, wherein n is 12.

4. A compound of the structure

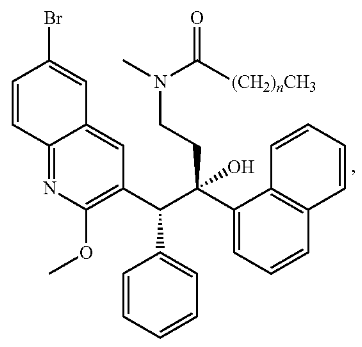

wherein n is an integer from 3 to 18.

5. The compound of claim 4, wherein n is 12.

6. A method for reducing the likelihood of tumor metastasis and tumor recurrence in a patient, the method comprising:

obtaining a biological sample of a cancer from the patient;

determining, or having determined, the level of biomarkers in the biological sample of a ATP-related metastasis gene-signature consisting of ABCA2, ATP5F1C, COX20, NDUFA2 and UQCRB;

comparing the determined level to a threshold level for the biomarkers;

confirming the determined level exceeds the threshold level; and administering a pharmaceutically effective amount of composition containing an active compound having the structure:

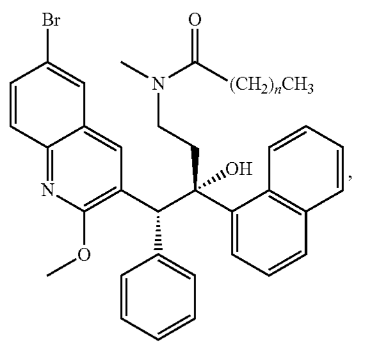
wherein n is an integer from 3 to 18.
7. The method of claim 6, wherein n is an integer from 5 to 14.
8. The method of claim 6, wherein n is 12.
* * * * *